(12) United States Patent
Fischer et al.

(10) Patent No.: US 9,474,524 B2
(45) Date of Patent: *Oct. 25, 2016

(54) PACKAGED ANTIMICROBIAL MEDICAL DEVICE HAVING IMPROVED SHELF LIFE AND METHOD OF PREPARING SAME

(75) Inventors: Jerry Fischer, Warren, NJ (US); Howard Scalzo, Kenilworth, NJ (US); Henry Pokropinski, Jr., South River, NJ (US)

(73) Assignee: Ethicon, Inc., Somerville, NJ (US)

( * ) Notice: Subject to any disclaimer, the term of this patent is extended or adjusted under 35 U.S.C. 154(b) by 351 days.

This patent is subject to a terminal disclaimer.

(21) Appl. No.: 13/501,063

(22) PCT Filed: Jun. 29, 2010

(86) PCT No.: PCT/US2010/040405
§ 371 (c)(1),
(2), (4) Date: Jul. 12, 2012

(87) PCT Pub. No.: WO2011/008547
PCT Pub. Date: Jan. 20, 2011

(65) Prior Publication Data
US 2012/0267263 A1    Oct. 25, 2012

Related U.S. Application Data

(63) Continuation of application No. 12/493,992, filed on Jun. 29, 2009, now Pat. No. 8,112,973, which is a continuation-in-part of application No. 12/415,600, filed on Mar. 31, 2009, which is a continuation-in-part (Continued)

(51) Int. Cl.
*B65D 81/24* (2006.01)
*B65B 55/02* (2006.01)
(Continued)

(52) U.S. Cl.
CPC ... *A61B 17/06114* (2013.01); *A61B 17/06138* (2013.01); *A61L 2/232* (2013.01);
(Continued)

(58) Field of Classification Search
CPC .................. A61B 17/06114; A61B 17/06138; A61B 17/06166; A61B 17/04; A61B 19/02; A61L 2/232; A61L 17/005; B65D 85/00; B65D 73/00

USPC ................................ 206/63.3, 380, 480, 204
See application file for complete search history.

(56) References Cited

U.S. PATENT DOCUMENTS

| 809,725 A | 1/1906 | Neff |
| 2,917,878 A | 12/1958 | Carnaruis et al. |

(Continued)

FOREIGN PATENT DOCUMENTS

| AU | 52834/86 B | 2/1987 |
| CA | 2185056 A1 | 3/1997 |

(Continued)

OTHER PUBLICATIONS

U.S. Appl. No. 11/301,365, filed Dec. 13, 2005.
(Continued)

*Primary Examiner* — Andrew Perreault
(74) *Attorney, Agent, or Firm* — Roberts Mlotkowski Safran Cole & Calderon, P.C.

(57) ABSTRACT

A method of making a packaged antimicrobial suture having improved shelf life. The method comprising the steps of providing an inner package having a source of antimicrobial agent, providing an adsorbent material effective to adsorb a portion of the antimicrobial agent over time, positioning a suture within the inner package, the suture comprising one or more surfaces, covering the inner package with an outer package having an inner surface and subjecting the suture, the inner package and the inner surface of the outer package to time, temperature and pressure conditions sufficient to vapor transfer an effective amount of the antimicrobial agent from the antimicrobial agent source to the suture and the inner package, thereby substantially inhibiting bacterial colonization on the suture and the inner package, wherein the packaged antimicrobial suture exhibits improved shelf life. A packaged antimicrobial suture and a method of increasing the shelf life of a packaged antimicrobial medical device are also provided.

24 Claims, 14 Drawing Sheets

Related U.S. Application Data of application No. 11/301,365, filed on Dec. 13, 2005, now Pat. No. 7,513,093, and a continuation-in-part of application No. 11/301,364, filed on Dec. 13, 2005, now Pat. No. 8,133,437, which is a continuation-in-part of application No. 10/808,669, filed on Mar. 25, 2004, now abandoned, which is a continuation of application No. 10/603,317, filed on Jun. 25, 2003, now abandoned, which is a continuation-in-part of application No. 10/367,497, filed on Feb. 15, 2003, now abandoned.

(60) Provisional application No. 60/416,114, filed on Oct. 4, 2002.

(51) Int. Cl.
 A61B 17/06 (2006.01)
 A61L 2/232 (2006.01)
 A61L 17/00 (2006.01)
 A61B 17/00 (2006.01)

(52) U.S. Cl.
 CPC ........ *A61L 17/005* (2013.01); *A61B 17/06166* (2013.01); *A61B 2017/00526* (2013.01); *A61B 2017/00889* (2013.01); *A61B 2017/06142* (2013.01); *A61B 2050/314* (2016.02); *A61L 2202/24* (2013.01); *A61L 2300/404* (2013.01)

(56) References Cited

U.S. PATENT DOCUMENTS

| | | |
|---|---|---|
| 2,947,282 A | 8/1960 | Brown |
| 3,068,864 A | 12/1962 | Tietze |
| 3,202,273 A | 8/1965 | Riall |
| 3,613,879 A | 10/1971 | Kemble |
| 3,629,477 A | 12/1971 | Model et al. |
| 3,642,003 A | 2/1972 | Kurtz |
| 3,726,057 A | 4/1973 | Kemble |
| 3,767,362 A | 10/1973 | Griffin et al. |
| 3,815,315 A | 6/1974 | Glick |
| 3,839,297 A | 10/1974 | Wasserman et al. |
| 3,862,304 A | 1/1975 | Kurtz |
| 3,896,812 A | 7/1975 | Kurts |
| 3,939,971 A | 2/1976 | Tulis |
| 3,991,766 A | 11/1976 | Schmitt et al. |
| 4,024,871 A | 5/1977 | Stephenson |
| 4,027,676 A | 6/1977 | Mattei |
| 4,105,034 A | 8/1978 | Shalaby et al. |
| 4,120,395 A | 10/1978 | Mandel et al. |
| 4,126,221 A | 11/1978 | Cerwin |
| 4,185,637 A | 1/1980 | Mattei |
| 4,201,216 A | 5/1980 | Mattei |
| 4,230,663 A | 10/1980 | Forstrom et al. |
| 4,476,590 A | 10/1984 | Scales et al. |
| 4,482,053 A | 11/1984 | Alpern et al. |
| 4,603,538 A | 8/1986 | Shave |
| 4,605,564 A | 8/1986 | Kulla et al. |
| 4,615,705 A | 10/1986 | Scales et al. |
| 4,728,323 A | 3/1988 | Matson |
| 4,846,844 A | 7/1989 | De Leon et al. |
| 4,853,978 A | 8/1989 | Stockum |
| 4,856,504 A | 8/1989 | Yamamoto et al. |
| 4,946,043 A | 8/1990 | Roshdy et al. |
| 4,952,419 A | 8/1990 | De Leon et al. |
| 4,967,902 A | 11/1990 | Sobel et al. |
| 5,019,096 A | 5/1991 | Fox, Jr. et al. |
| 5,037,429 A | 8/1991 | Hermes et al. |
| 5,052,551 A | 10/1991 | Cerwin et al. |
| 5,066,328 A | 11/1991 | Zlotnik |
| 5,091,442 A | 2/1992 | Milner |
| 5,128,101 A | 7/1992 | Boynton |
| 5,131,534 A | 7/1992 | Brown et al. |
| 5,154,283 A | 10/1992 | Brown |
| 5,165,913 A | 11/1992 | Hill et al. |
| 5,180,605 A | 1/1993 | Milner |
| 5,213,210 A | 5/1993 | Cascio et al. |
| 5,222,978 A | 6/1993 | Kaplan et al. |
| 5,230,424 A | 7/1993 | Alpern et al. |
| 5,261,421 A | 11/1993 | Milner |
| 5,284,240 A | 2/1994 | Alpern et al. |
| 5,295,979 A | 3/1994 | DeLaurentis et al. |
| 5,359,831 A | 11/1994 | Brown et al. |
| 5,366,081 A | 11/1994 | Kaplan et al. |
| 5,464,580 A | 11/1995 | Popescu et al. |
| 5,468,252 A | 11/1995 | Kaplan et al. |
| 5,468,562 A | 11/1995 | Farivar et al. |
| 5,474,797 A | 12/1995 | Sioshansi et al. |
| 5,518,730 A | 5/1996 | Fuisz |
| 5,529,175 A | 6/1996 | Brunken |
| 5,534,288 A | 7/1996 | Gruskin et al. |
| 5,555,976 A | 9/1996 | Pernot |
| 5,556,699 A | 9/1996 | Niira et al. |
| 5,562,211 A | 10/1996 | Simons et al. |
| 5,607,681 A | 3/1997 | Galley et al. |
| 5,623,810 A | 4/1997 | Dey et al. |
| 5,708,023 A | 1/1998 | Modak et al. |
| 5,722,992 A | 3/1998 | Goldmann |
| 5,756,145 A | 5/1998 | Darouiche |
| 5,772,640 A | 6/1998 | Modak et al. |
| 5,804,628 A | 9/1998 | Busnel et al. |
| 5,853,745 A | 12/1998 | Darouiche |
| 5,868,244 A | 2/1999 | Ivanov et al. |
| 5,889,075 A | 3/1999 | Roby et al. |
| 5,902,283 A | 5/1999 | Darouiche |
| 5,906,273 A | 5/1999 | Pohle et al. |
| 5,906,825 A | 5/1999 | Seabrook et al. |
| 5,945,153 A | 8/1999 | Dearnaley |
| 5,965,610 A | 10/1999 | Modak et al. |
| 5,968,207 A | 10/1999 | Li |
| 5,972,008 A | 10/1999 | Kalinski et al. |
| 5,985,934 A | 11/1999 | Gaffney et al. |
| 5,997,815 A | 12/1999 | Anders et al. |
| 6,021,625 A | 2/2000 | Cerwin et al. |
| 6,034,010 A | 3/2000 | Cartwright et al. |
| 6,037,386 A | 3/2000 | Modak et al. |
| 6,047,815 A | 4/2000 | Cerwin et al. |
| 6,083,208 A | 7/2000 | Modak et al. |
| 6,087,415 A | 7/2000 | Vamderlaan et al. |
| 6,093,414 A | 7/2000 | Capelli |
| 6,106,505 A | 8/2000 | Modak et al. |
| 6,135,272 A | 10/2000 | Sobel et al. |
| 6,165,920 A | 12/2000 | Rubin et al. |
| 6,200,583 B1 | 3/2001 | Sibata et al. |
| 6,224,579 B1 | 5/2001 | Modak et al. |
| 6,238,686 B1 | 5/2001 | Burrell et al. |
| 6,260,699 B1 | 7/2001 | Kaplan et al. |
| 6,315,788 B1 | 11/2001 | Roby |
| 6,420,455 B1 | 7/2002 | Landgrebe et al. |
| 6,475,434 B1 | 11/2002 | Darouiche |
| 6,481,568 B1 | 11/2002 | Cerwin et al. |
| 6,494,898 B1 | 12/2002 | Roby et al. |
| 6,495,100 B1 | 12/2002 | Lin et al. |
| 6,706,024 B2 | 3/2004 | Modak et al. |
| 6,837,027 B2 | 1/2005 | Hickey |
| 6,878,757 B2 | 4/2005 | Roby |
| 6,915,623 B2 | 7/2005 | Dey et al. |
| 6,916,480 B2 | 7/2005 | Anderson et al. |
| 7,070,044 B2 | 7/2006 | Rosenfeld |
| 7,215,401 B2 | 5/2007 | Ishiyama et al. |
| 7,275,640 B2 | 10/2007 | Bourne et al. |
| 7,357,949 B2 | 4/2008 | Trogolo et al. |
| 7,513,093 B2 | 4/2009 | Scalzo et al. |
| 7,651,661 B2 | 1/2010 | Raad et al. |
| 8,069,980 B2 | 12/2011 | Stopek et al. |
| 8,112,973 B2 | 2/2012 | Fischer et al. |
| 8,133,437 B2 | 3/2012 | Scalzo et al. |
| 8,156,718 B2 | 4/2012 | Scalzo et al. |
| 2001/0010016 A1 | 7/2001 | Modak et al. |
| 2001/0016589 A1 | 8/2001 | Modak et al. |
| 2001/0024661 A1 | 9/2001 | Modak et al. |
| 2002/0012760 A1 | 1/2002 | Barry et al. |
| 2002/0055759 A1 | 5/2002 | Shibuya |

(56) References Cited

U.S. PATENT DOCUMENTS

| | | |
|---|---|---|
| 2003/0108761 A1 | 6/2003 | Eddlemon |
| 2003/0138347 A1 | 7/2003 | Lin |
| 2004/0068293 A1 | 4/2004 | Scalzo et al. |
| 2004/0068294 A1 | 4/2004 | Scalzo et al. |
| 2004/0220614 A1 | 11/2004 | Scalzo et al. |
| 2005/0033251 A1 | 2/2005 | Toreki et al. |
| 2005/0101993 A1 | 5/2005 | Scalzo et al. |
| 2006/0091035 A1 | 5/2006 | Scalzo et al. |
| 2006/0231443 A1 | 10/2006 | Jonasson et al. |
| 2008/0171972 A1 | 7/2008 | Stopek |
| 2009/0301033 A1 | 12/2009 | Scalzo et al. |
| 2010/0036359 A1 | 2/2010 | Stopek et al. |
| 2010/0078336 A1 | 4/2010 | Reyhan et al. |
| 2010/0116694 A1 | 5/2010 | Stopek et al. |
| 2010/0163435 A1 | 7/2010 | Fischer et al. |
| 2012/0199502 A1 | 8/2012 | Scalzo et al. |
| 2012/0227360 A1 | 9/2012 | Scalzo et al. |
| 2012/0267263 A1 | 10/2012 | Fischer et al. |
| 2013/0193008 A1 | 8/2013 | Reyhan et al. |
| 2013/0193009 A1 | 8/2013 | Scalzo et al. |
| 2013/0264226 A1 | 10/2013 | Prikril et al. |

FOREIGN PATENT DOCUMENTS

| | | |
|---|---|---|
| CN | 2115083 U | 9/1992 |
| CN | 2190968 Y | 3/1995 |
| CN | 1125622 A | 7/1996 |
| EP | 0470443 A2 | 2/1992 |
| EP | 0471441 A1 | 2/1992 |
| EP | 0761243 A1 | 3/1997 |
| EP | 1159972 A2 | 12/2001 |
| GB | 809725 A | 3/1959 |
| JP | 49-111794 A | 10/1974 |
| JP | 8-164190 A | 6/1996 |
| JP | 10-504756 T | 5/1998 |
| JP | 11-500330 T | 1/1999 |
| JP | 2000-237289 A | 5/2000 |
| TW | 408011 B | 10/2000 |
| TW | 446822 B | 7/2001 |
| WO | 98/09667 A1 | 3/1998 |
| WO | 00/44414 A1 | 8/2000 |
| WO | 01/28601 A1 | 4/2001 |
| WO | 2004032704 A2 | 4/2004 |
| WO | 2008/045338 A2 | 4/2008 |
| WO | 2008045338 A2 | 4/2008 |
| WO | WO 2010/117802 A1 | 10/2010 |
| WO | WO 2011/008547 A1 | 1/2011 |

OTHER PUBLICATIONS

U.S. Appl. No. 12/417,518, filed Apr. 2, 2009.
U.S. Appl. No. 12/415,600, filed Mar. 31, 2009.
U.S. Appl. No. 11/301,364, filed Dec. 13, 2005.
U.S. Appl. No. 12/493,992, filed Jun. 29, 2009.
PCT Application No. PCT/US2010/029233 filed Mar. 30, 2010.
US Application No. PCT/US2010/040405 filed Jun. 29, 2010.
U.S. Appl. No. 13/419,377, filed Mar. 13, 2012.
U.S. Appl. No. 13/449,184, filed Apr. 17, 2012.
U.S. Appl. No. 61/621,337, filed Apr. 6, 2012.
U.S. Appl. No. 13/727,340, filed Dec. 26, 2012.
International Search Report of International Application No. PCT/US2010/029233.
Database EMBASE on STN, AN 2003062. Barbolt T.A. "Chemistry and Safety of Triclosan, and Its Use as an Antimicrobial Coating on Coated VICRYL. Plus Antibacterial Suture (Coated Polyglactin 910 Suture with Triclosan)". Surgical Infections, May 2002, vol. 3, No. 3, Supplement 1, pp. S-45-S-53, see abstract.
Database ACS on STN, AN 133: 366471. Anuzis et al. "Acetate Antimicrobial Threads". LT 4568 B, Oct. 25, 1999 (Oct. 25, 1999), abstract.
Josephine J. Braid et al., "The antibacterial activity of triclosan-impregnated storage boxes against *Staphylococcus aureus, Escherichia colil*, Pseudomonas aeruginosa, Bacillus cereus and Shewanella putrefaciens in conditions simulating domestic use" Journal of Antimocrobial Chemotherapy (2002) vol. 49 pp. 87-94.
Bhargava, H. et al "American Journal of Infection Control" pp. 209-218, Jun. 1996. Abstract only.
Robert Cerwin, U.S. Appl. No. 60/416,114, filed Oct. 4, 2002.
Howard Scalzo, U.S. Appl. No. 10/367,497, filed Feb. 15, 2003.
Howard Scalzo , U.S. Appl. No. 10/367,565, filed Feb. 15, 2003.
Howard Scalzo, U.S. Appl. No. 10/603,317, filed Jun. 25, 2003.
Howard Scalzo, U.S. Appl. No. 10/808,669, filed Mar. 25, 2004.
Howard Scalzo, U.S. Appl. No. 11/301,365, filed Dec. 13, 2005.
Howard Scalzo, U.S. Appl. No. 11/301,364, filed Dec. 13, 2005.
Mehmet Reyhan, U.S. Appl. No. 12/415,600, filed Mar. 31, 2009.
Howard Scalzo, U.S. Appl. No. 12/417,518, filed Apr. 2, 2009.
Jerry Fischer, U.S. Appl. No. 12/493,992, filed Jun. 29, 2009.
Mehmet Reyhan, PCT Application No. PCT/US2010/029233 filed Mar. 30, 2010.
Jerry Fischer, PCT Application No. PCT/US2010/040405 filed Jun. 29, 2010.
Howard Scalzo, U.S. Appl. No. 13/419,377, filed Mar. 13, 2012.
Michael David Prikril, U.S. Appl. No. 61/621,337, filed Apr. 6, 2012.
Jerry Fischer, U.S. Appl. No. 13/501,063, filed Apr. 9, 2012.
Howard Scalzo, U.S. Appl. No. 13/449,184, filed Apr. 17, 2012.
Michael David Prikril, U.S. Appl. No. 13/727,340, filed Dec. 26, 2012.
Mehmet Reyhan, U.S. Appl. No. 13/801,819, filed Mar. 13, 2013.
Howard Scalzo, U.S. Appl. No. 13/802,007, filed Mar. 13, 2013.
International Search Report of International Application No. PCT/US2010/040405.
U.S. Appl. No. 60/416,114, filed Oct. 4, 2002.
U.S. Appl. No. 10/367,497, filed Feb. 15, 2003.
U.S. Appl. No. 10/367,565, filed Feb. 15, 2003.
U.S. Appl. No. 10/603,317, filed Jun. 25, 2003.
U.S. Appl. No. 10/808,669, filed Mar. 25, 2004.

PACKAGED ANTIMICROBIAL MEDICAL DEVICE HAVING IMPROVED SHELF LIFE AND METHOD OF PREPARING SAME

The present invention relates to an antimicrobial medical device and an antimicrobial packaged medical device and their methods of making.

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated within have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated. It is not apparent from the application at what temperature the sterilized, coated catheters were stored.

Most implantable medical devices are manufactured, sterilized and contained in packages until opened for use in a surgical procedure. During surgery, the opened package containing the medical device, packaging components contained therein, and the medical device, are exposed to the operating room atmosphere, where bacteria from the air may be introduced. Incorporating antimicrobial properties into the package and/or the packaging components contained therein substantially prevents bacterial colonization on the package and components once the package has been opened. The antimicrobial package and/or packaging components in combination with the incorporation of antimicrobial properties onto the medical device itself would substantially ensure an antimicrobial environment about the sterilized medical device.

Packaged medical devices having antimicrobial properties may exhibit a limited shelf life. Therefore, what is needed is a packaged antimicrobial medical device having an extended shelf life and methods for extending the shelf life of a packaged antimicrobial medical device.

In one aspect, disclosed herein is a method of making a packaged antimicrobial suture having improved shelf life. The method includes the steps of providing an inner package having a source of antimicrobial agent, providing an adsorbent material effective to adsorb a portion of the antimicrobial agent over time, positioning a suture within the inner package, the suture comprising one or more surfaces, covering the inner package with an outer package having an inner surface and subjecting the suture, the inner package and the inner surface of the outer package to time, temperature and pressure conditions sufficient to vapor transfer an effective amount of the antimicrobial agent from the antimicrobial agent source to the suture and the inner package, thereby substantially inhibiting bacterial colonization on the suture and the inner package, wherein the packaged antimicrobial suture exhibits improved shelf life.

In one embodiment, the adsorbent material is provided by coating the adsorbent material on at least a portion of one surface of the inner package.

In another embodiment, the adsorbent material is provided by placing an adsorbent substrate within the outer package.

In yet another embodiment, the adsorbent substrate is formed by coating a substrate with an adsorbent material.

In still yet another embodiment, the adsorbent substrate is formed of an adsorbent material.

In a further embodiment, the antimicrobial agent is selected from the group consisting of halogenated hydroxyl ethers, acyloxydiphenyl ethers, and combinations thereof.

In a still further embodiment, the effective amount of the antimicrobial agent transferred from the source of antimicrobial agent to the suture and the inner package is transferred during an ethylene oxide sterilization process.

In another embodiment, the step of subjecting the suture, the inner package and the inner surface of the outer package to conditions sufficient to vapor transfer an effective amount of the antimicrobial agent comprises the steps of placing the outer package having the inner package and the suture therein in a sterilization unit, heating the sterilization unit to a first temperature, adjusting the pressure in the sterilization unit to a first pressure value, injecting steam into the sterilization unit to expose the inner surface of the outer package, the inner package and the suture to water vapor for a first period of time, adjusting the pressure within the sterilization unit to a second pressure value, introducing a chemical sterilization agent into the sterilization unit, maintaining the chemical sterilization agent in the sterilization unit for a second period of time to render a sufficient amount of microorganisms non-viable, removing residual moisture and chemical sterilization agent from the suture, and drying the packaged antimicrobial suture to a desired moisture level.

In yet another embodiment, the inner package comprises a universal envelope formed from a paperboard stock having at least one surface coated with an adsorbent material.

In yet still another embodiment, the inner package comprises a containment compartment having an outer cover, the outer cover having one surface coated with an adsorbent material.

In a further embodiment, the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

The present invention is also directed to a method of increasing the shelf life of a packaged antimicrobial medical device. The method includes the steps of providing an inner package having a source of antimicrobial agent, providing an adsorbent material effective to adsorb a portion of the antimicrobial agent over time, positioning a medical device within the inner package, the medical device comprising one or more surfaces, covering the inner package with an outer package having an inner surface and subjecting the medical device, the inner package and the inner surface of the outer package to time, temperature and pressure conditions sufficient to vapor transfer an effective amount of the antimicrobial agent from the antimicrobial agent source to the medical device and the inner package, thereby substantially inhibiting bacterial colonization on the medical device and the inner package, wherein the packaged antimicrobial medical device exhibits improved shelf life.

The present invention also relates to a packaged antimicrobial suture having improved shelf life. The packaged antimicrobial suture includes an inner package having a source of antimicrobial agent and an adsorbent material effective to adsorb a portion of the antimicrobial agent over time, a suture positioned within the inner package, the suture comprising one or more surfaces and an outer package having an inner surface, the outer package having the inner package positioned within, wherein the suture, the inner package and the inner surface of the outer package are subjected to time, temperature and pressure conditions sufficient to vapor transfer an effective amount of the antimicrobial agent from the antimicrobial agent source to the suture and the inner package, thereby substantially inhibiting bacterial colonization on the suture and the inner package.

In one embodiment the packaged antimicrobial suture exhibits improved shelf life.

The present invention is also directed to a packaged medical device. The packaged antimicrobial device includes an inner package having a source of antimicrobial agent and an adsorbent material effective to adsorb a portion of the antimicrobial agent over time, a medical device positioned within the inner package, the medical device comprising one or more surfaces; and an outer package having an inner surface, the outer package having the inner package positioned within, wherein the medical device, the inner package and the inner surface of the outer package are subjected to time, temperature and pressure conditions sufficient to vapor transfer an effective amount of the antimicrobial agent from the antimicrobial agent source to the medical device and the inner package, thereby substantially inhibiting bacterial colonization on the medical device and the inner package.

The invention is further explained in the description that follows with reference to the drawings illustrating, by way of non-limiting examples, various embodiments of the invention wherein.

Figure 7:
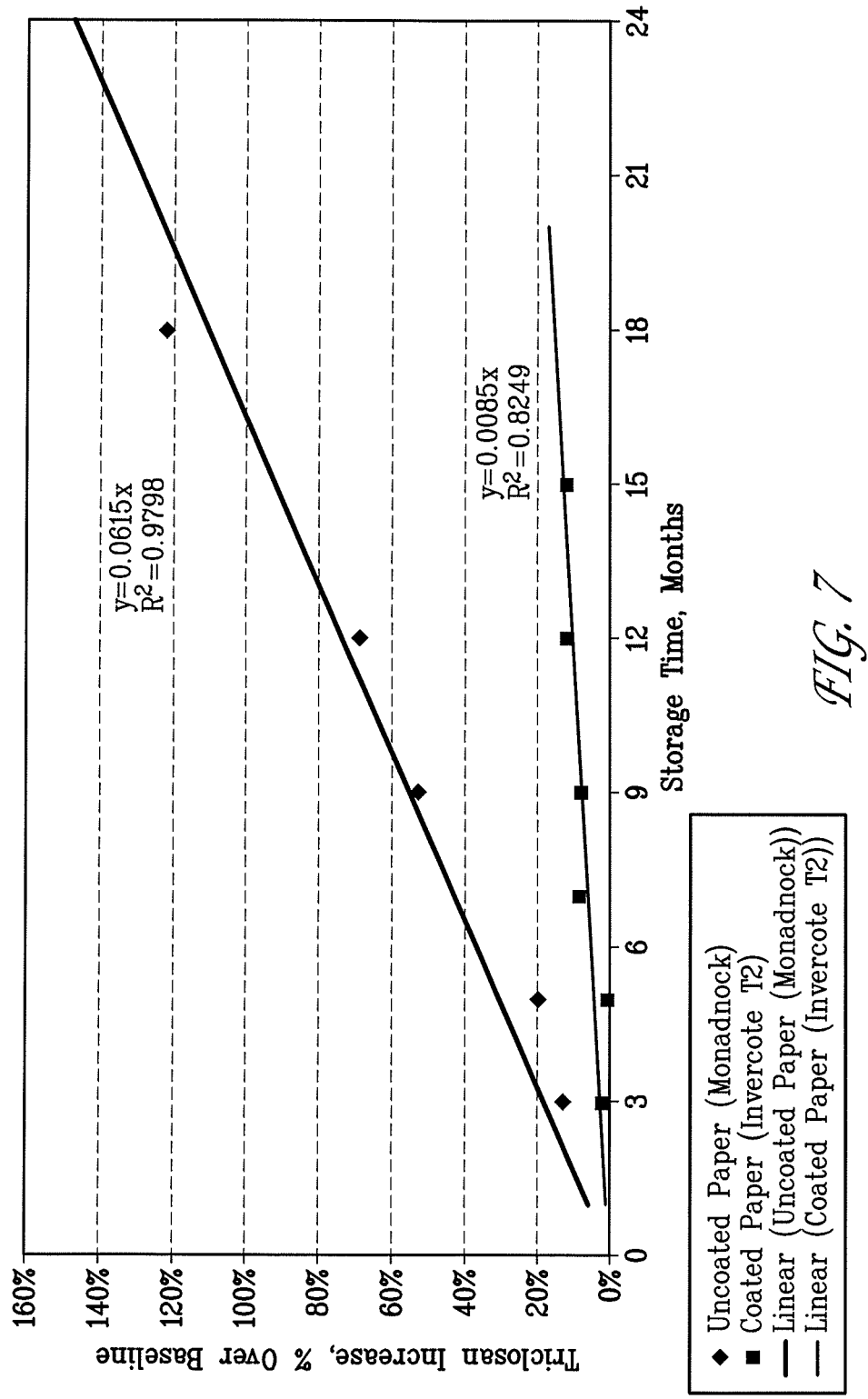

FIG. 7 presents a comparison of triclosan increase as a function of storage time at 25° C. for an adsorbent-containing suture package, of the type disclosed herein, versus a suture package without adsorbent.

Figure 8:
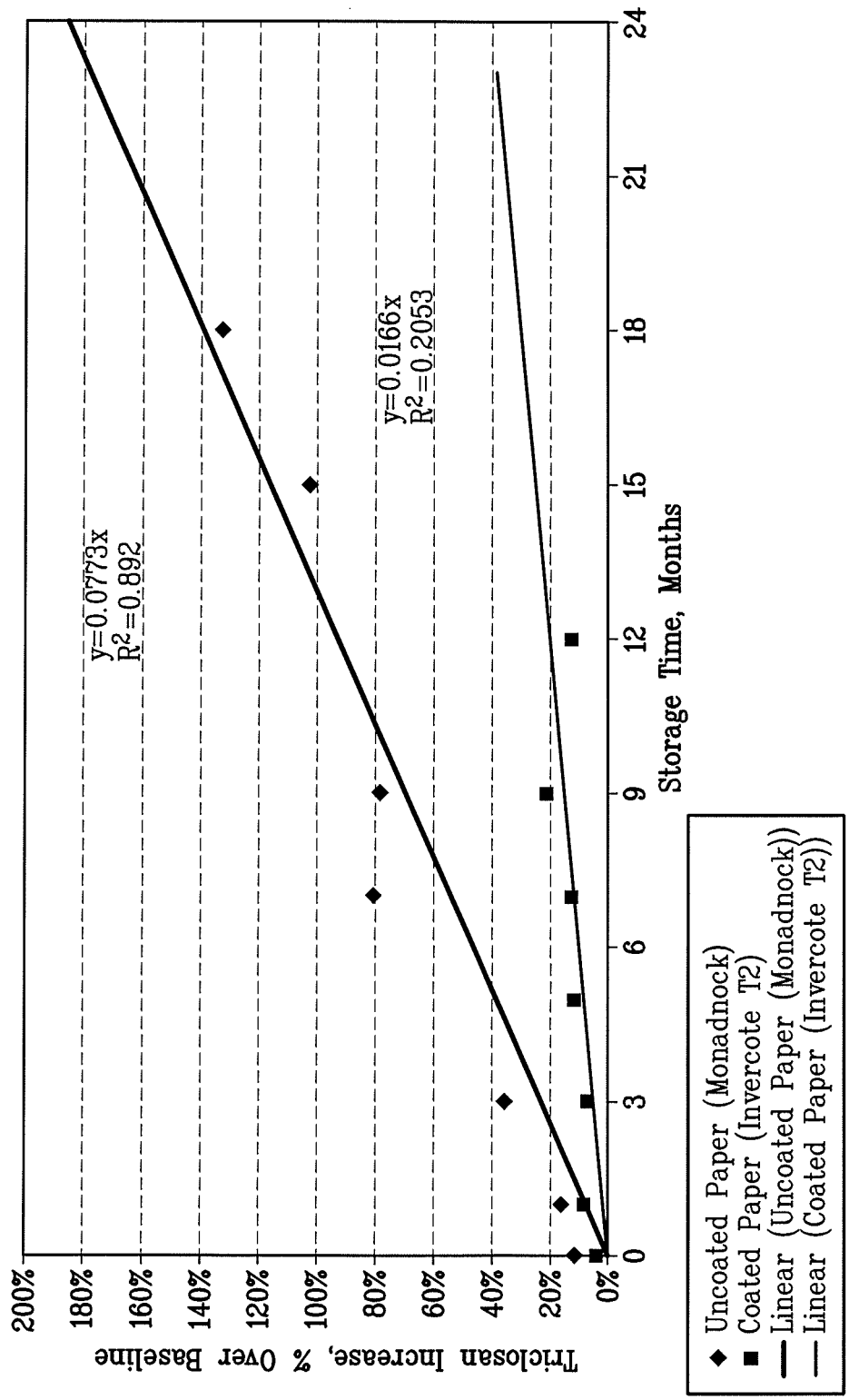

FIG. 8 presents a comparison of triclosan increase as a function of storage time at 25° C. for an adsorbent-containing suture package, of the type disclosed herein, versus a suture package without adsorbent.

Figure 9:
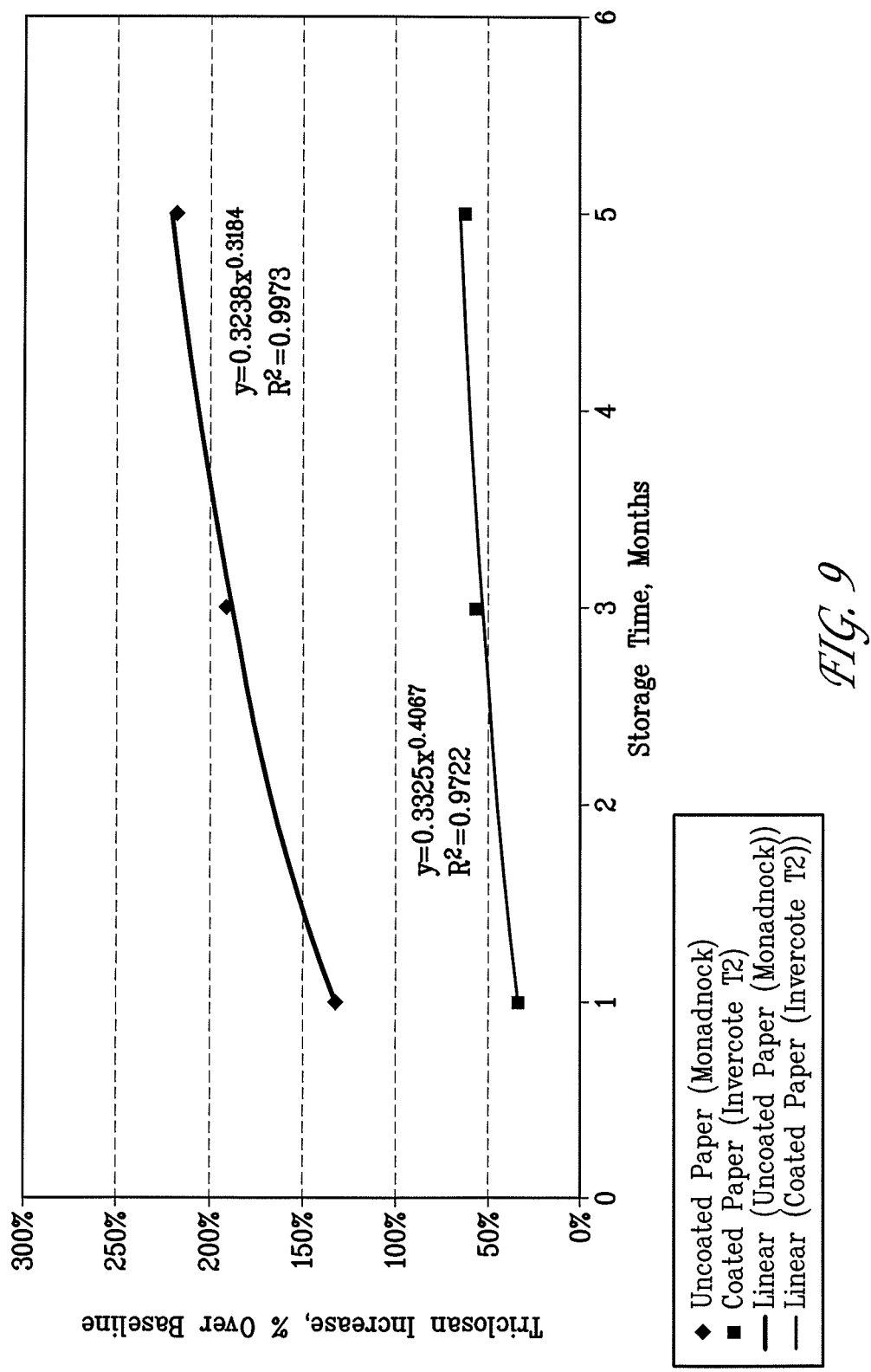

FIG. 9 presents a comparison of triclosan increase as a function of storage time at 50° C. for an adsorbent-containing suture package, of the type disclosed herein, versus a suture package without adsorbent.

Figure 10:
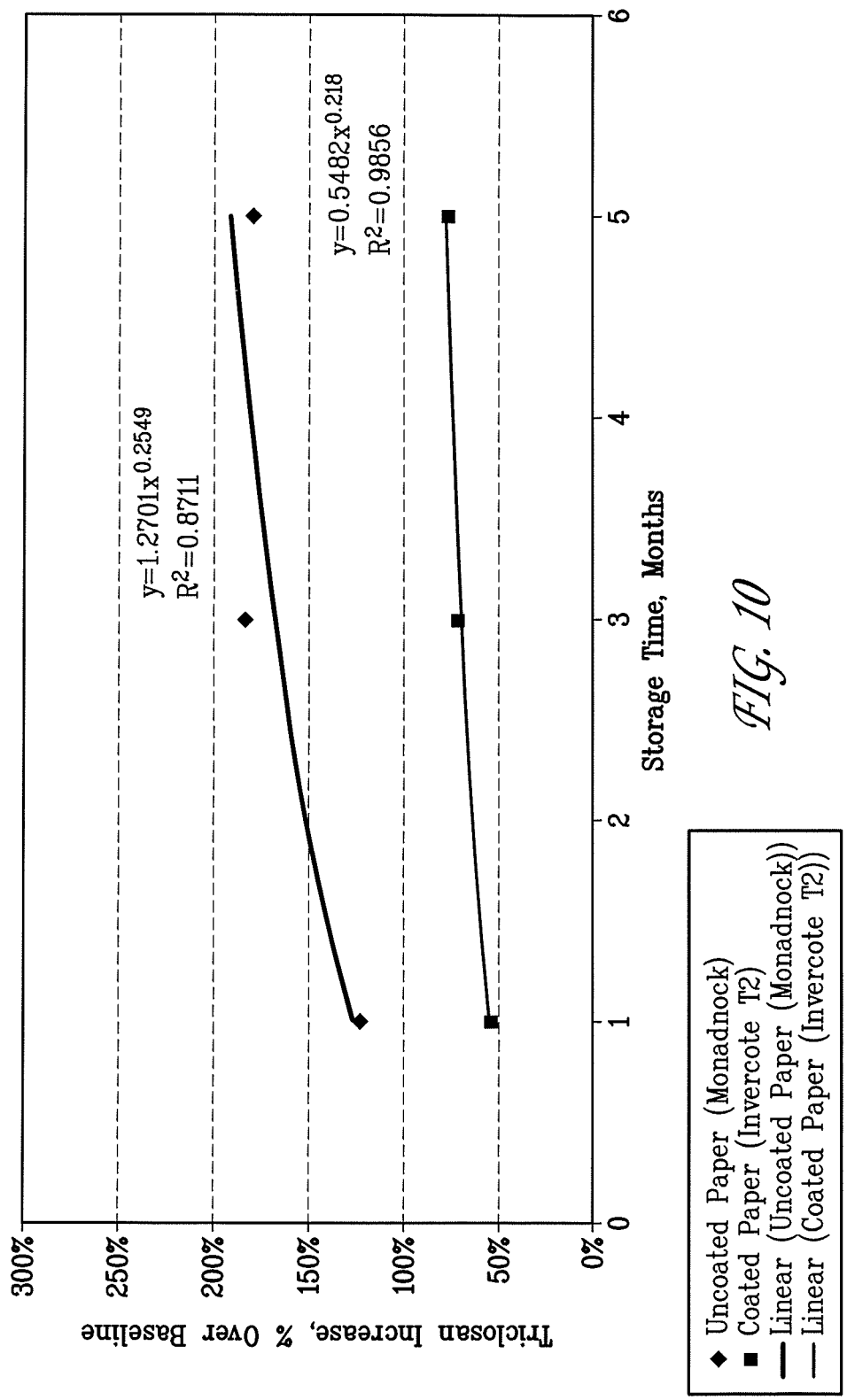

FIG. 10 presents a comparison of triclosan increase as a function of storage time at 50° C. for an adsorbent-containing suture package, of the type disclosed herein, versus a suture package without adsorbent.

Figure 11:
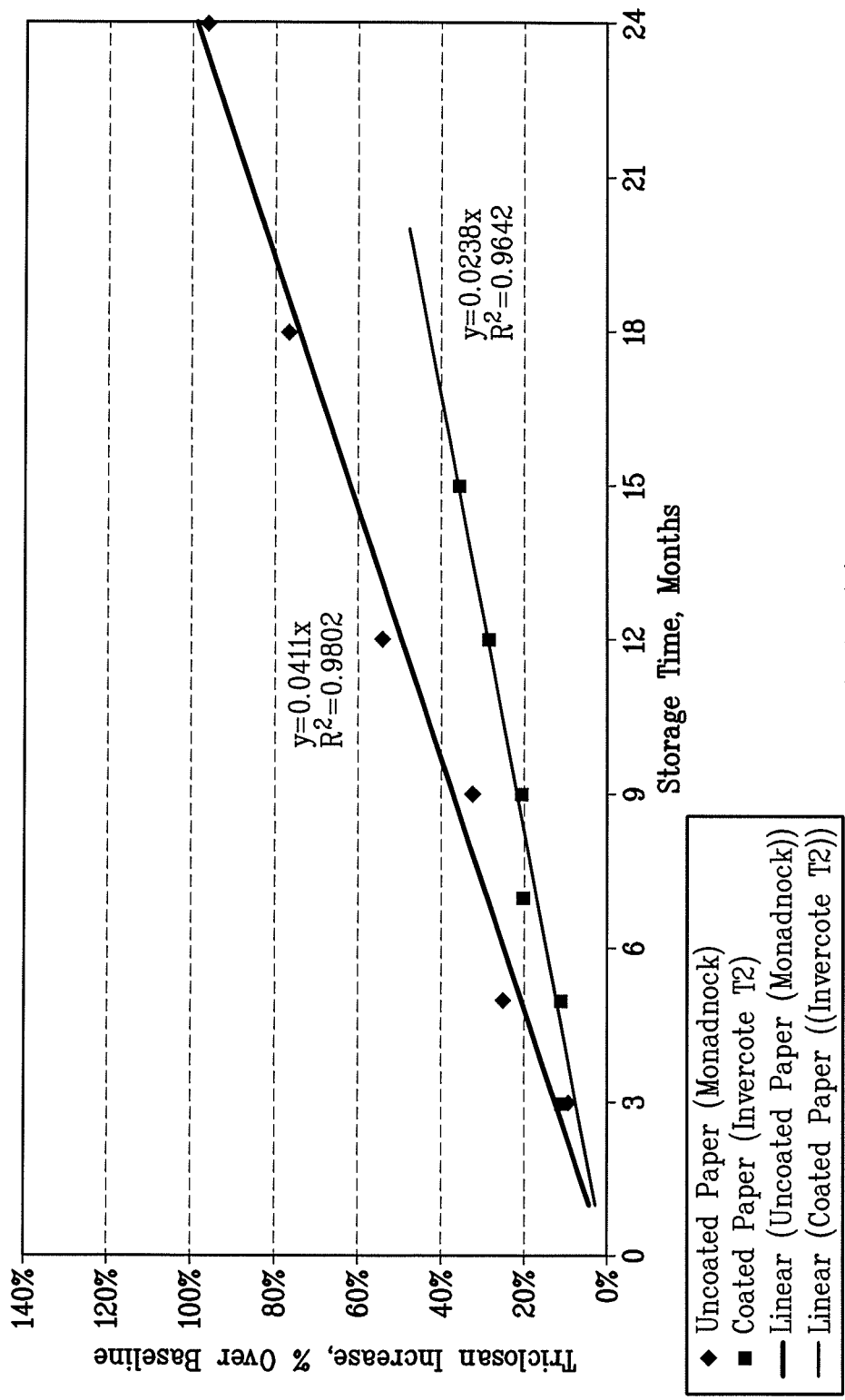

FIG. 11 presents a comparison of triclosan increase as a function of storage time at 25° C. for an adsorbent-containing suture package, of the type disclosed herein, versus a suture package without adsorbent.

Figure 12:
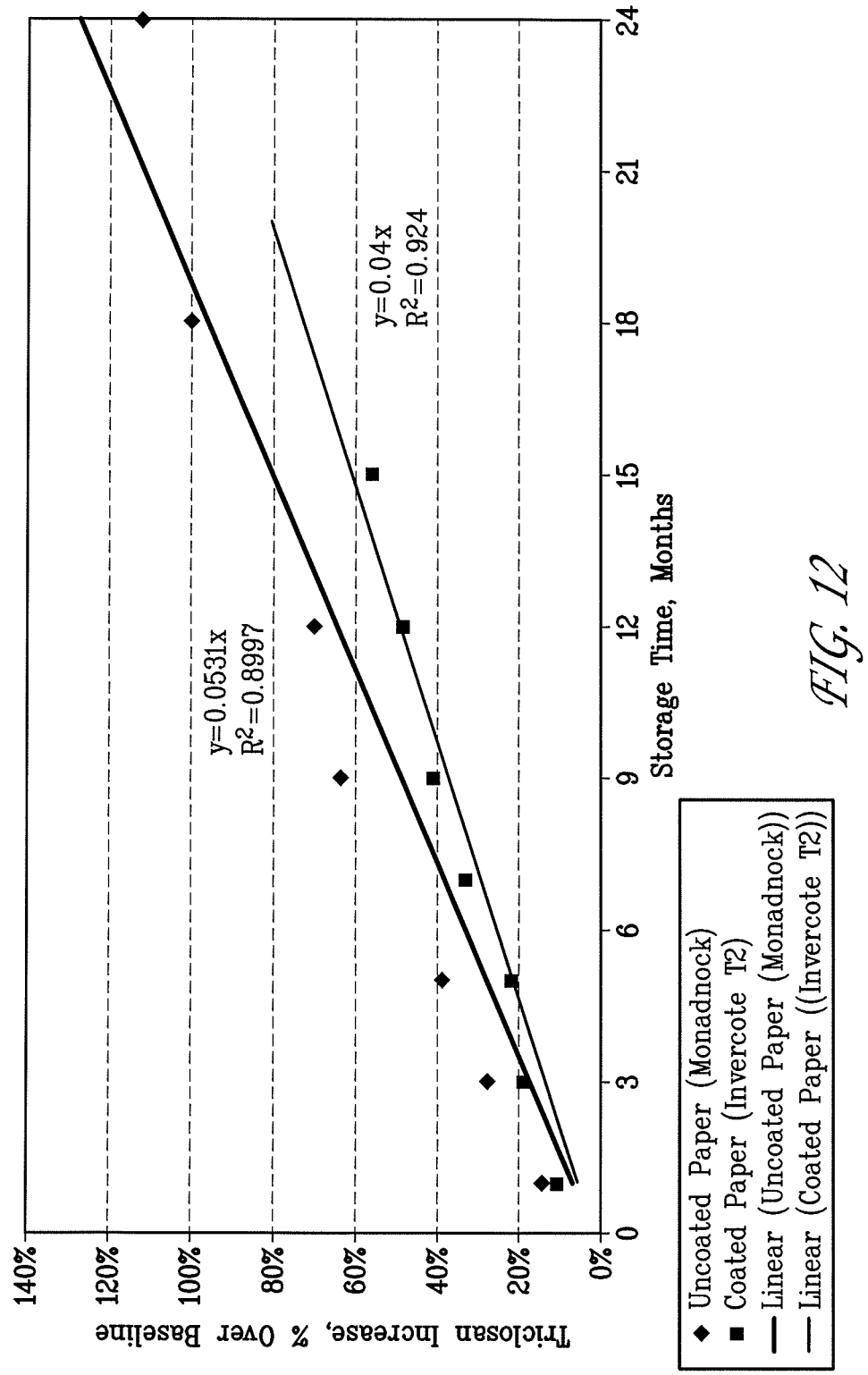

FIG. 12 presents a comparison of triclosan increase as a function of storage time at 25° C. for an adsorbent-containing suture package, of the type disclosed herein, versus a suture package without adsorbent.

Figure 13:
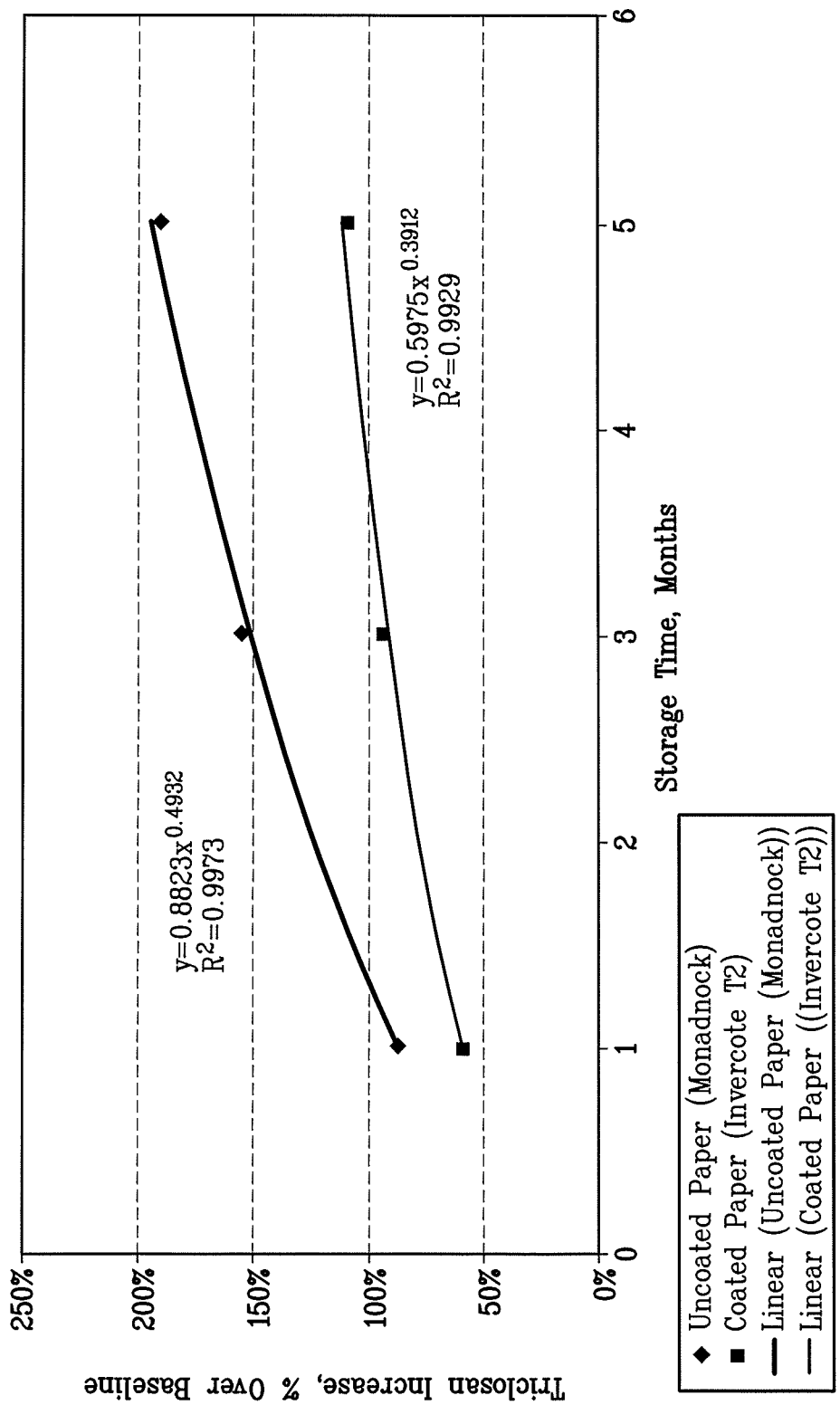

FIG. 13 presents a comparison of triclosan increase as a function of storage time at 50° C. for an adsorbent-containing suture package, of the type disclosed herein, versus a suture package without adsorbent.

Figure 14:
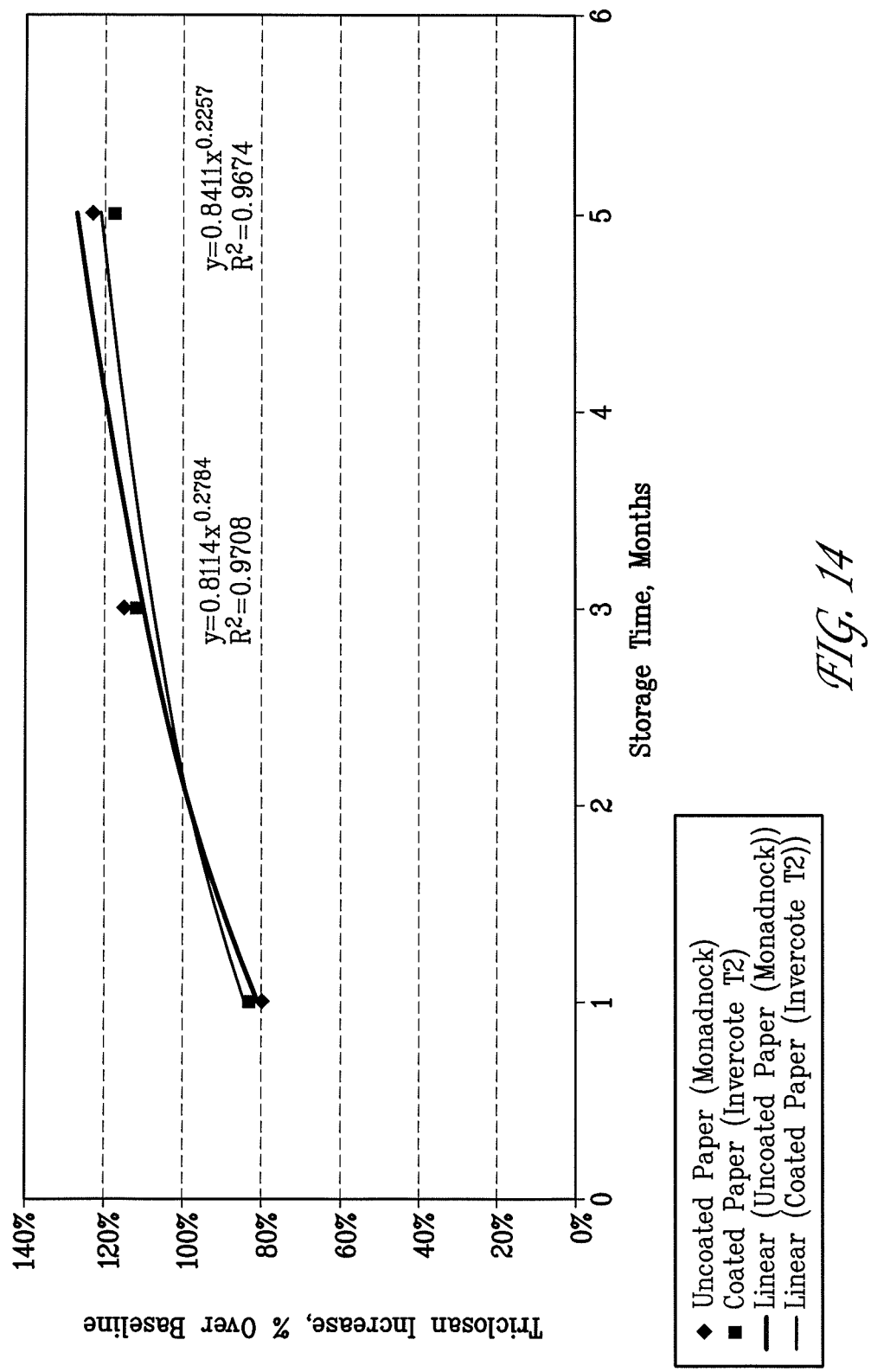

FIG. 14 presents a comparison of triclosan increase as a function of storage time at 50° C. for an adsorbent-containing suture package, of the type disclosed herein, versus a suture package without adsorbent.

Reference is now made to FIGS. 1-14 wherein like numerals are used to designate like elements throughout.

Figure 1:
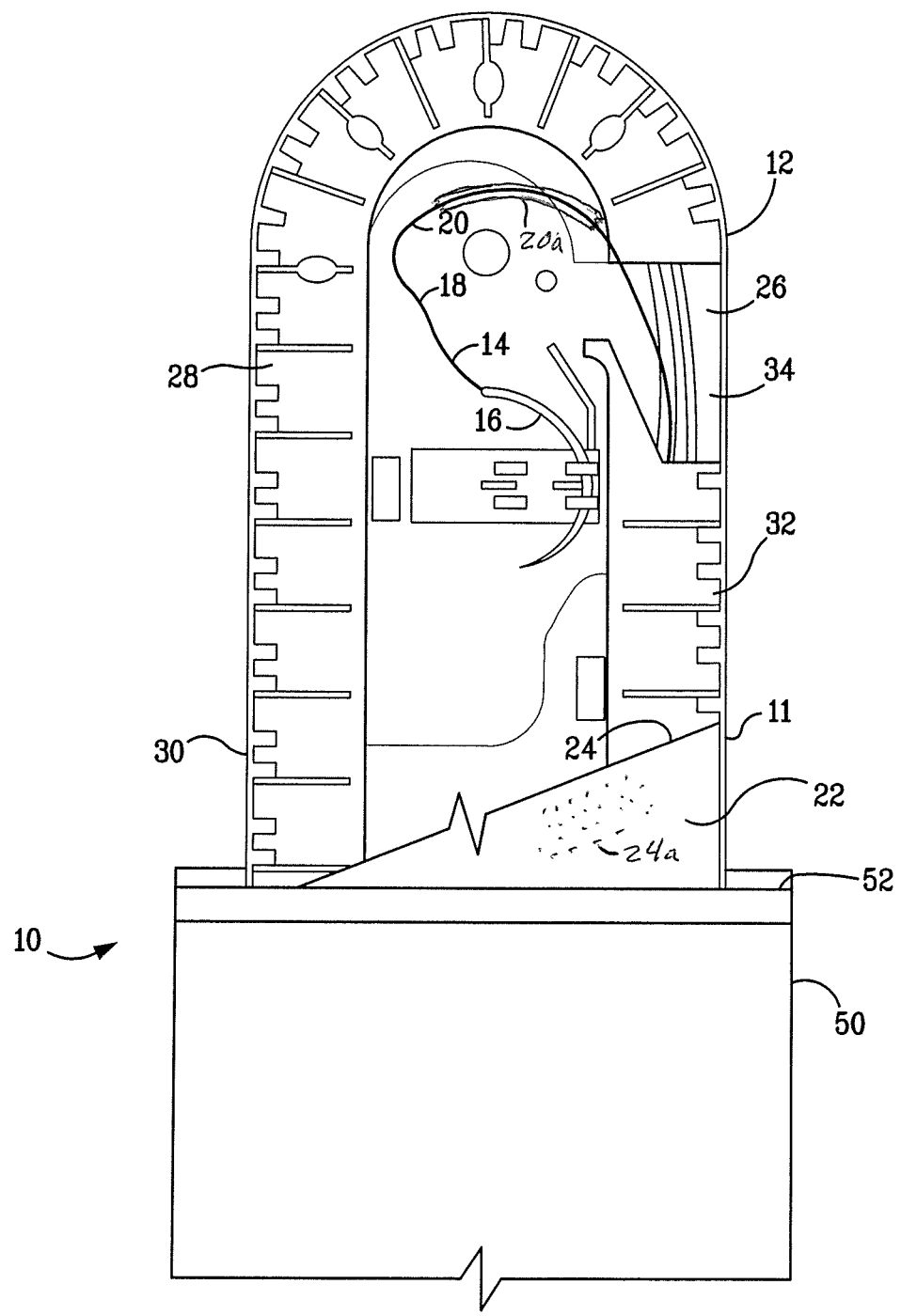
FIG. 1 is a top plan view of one form of a packaged antimicrobial medical device, in accordance herewith, wherein the medical device is a single needle and suture.

Referring now to FIG. 1, one embodiment of a packaged antimicrobial medical device 10 is shown. Packaged antimicrobial medical device 10 includes an inner package 11 having a source of antimicrobial agent. A medical device 14, which may be a needle 16 and suture 18 having one or more surfaces 20 is positioned within the inner package 11, which surfaces may be coated with said antimicrobial agent to form the antimicrobial source 20a in one embodiment. In one embodiment, inner package 11 comprises a containment compartment 12 and an outer cover 22, the outer cover 22 having one surface 24 that may be coated with an adsorbent material 24a. In one embodiment, the adsorbent material is effective to adsorb a portion of the antimicrobial agent over time. An outer package 50 having an inner surface 52 is provided to seal the inner package 11 when positioned within.

The containment compartment 12 of packaged antimicrobial medical device 10 includes a base member 26 and a channel cover member 28. Base member 26 includes a top side, bottom side, and an outer periphery 30. As shown, an outer cover 22 may be positioned upon channel cover member 28 and within outer periphery 30, to at least partially enclose medical device 14. The base member 26 may be a substantially flat substantially oval shaped member having a longitudinal axis. While in the case of packaged sutures, it may be desired that the base member 26 of packaged antimicrobial medical device 10 be oval shaped, other configurations can be used including circular, polygonal, square with rounded corners, and the like and combinations thereof and equivalents thereof. Channel cover 28 includes a top side, bottom side, periphery 32 and longitudinal axis.

The packaged antimicrobial medical device 10 of the present invention may be assembled in the following manner. Base member 26 is aligned with channel cover member 28 so that rivets, if employed are in alignment with the rivet receiving holes, and locating pins, if employed, are in alignment with corresponding openings. Also, winding pin openings, if employed, are aligned with corresponding openings. Then, channel cover member 28 is then mounted to base member 26 such that rivets, if employed, are inserted into and through corresponding holes and locating pins, if employed, are inserted through corresponding holes. The ends of the rivets, if employed, may be spread by using conventional techniques such as heating, ultrasonic treatments, and the like, so that the channel cover member 28 is firmly affixed to the base member 26. In this embodiment, when containment compartment 12 is so formed, a channel 34 is formed, which may advantageously house a wound suture 18.

Referring now to FIGS. 2-5, another embodiment of the packaged antimicrobial medical device 100 is shown. Packaged antimicrobial medical device 10 includes an inner package 111 having a source of antimicrobial agent. A medical device 114, which may be a needle 116 and suture 118 having one or more surfaces 120 is positioned within the inner package 111. In one embodiment, inner package 111 comprises a containment compartment 112 and an outer cover 122, the outer cover 122 having one surface 124 coated with an adsorbent material. In one embodiment, the adsorbent material is effective to adsorb a portion of the antimicrobial agent over time. An outer package 150 having an inner surface 152 is provided to seal the inner package 111 positioned within.

The containment compartment 112 of packaged antimicrobial medical device 100 includes a base member 126 and a plurality of channel cover tab members 128. Base member 126 includes a top side, bottom side, and an outer periphery 130. In one embodiment, an outer cover 122 may be positioned upon containment compartment 112 and within outer periphery 130, to at least partially enclose medical device 114.

The base member 126 may be a substantially flat substantially oval shaped member having a longitudinal axis. While in the case of packaged sutures, it may be desired that the base member 126 of packaged antimicrobial medical device 100 be oval shaped, although other configurations can be used including circular, polygonal, square with rounded corners, and the like and combinations thereof and equivalents thereof.

Figure 2:
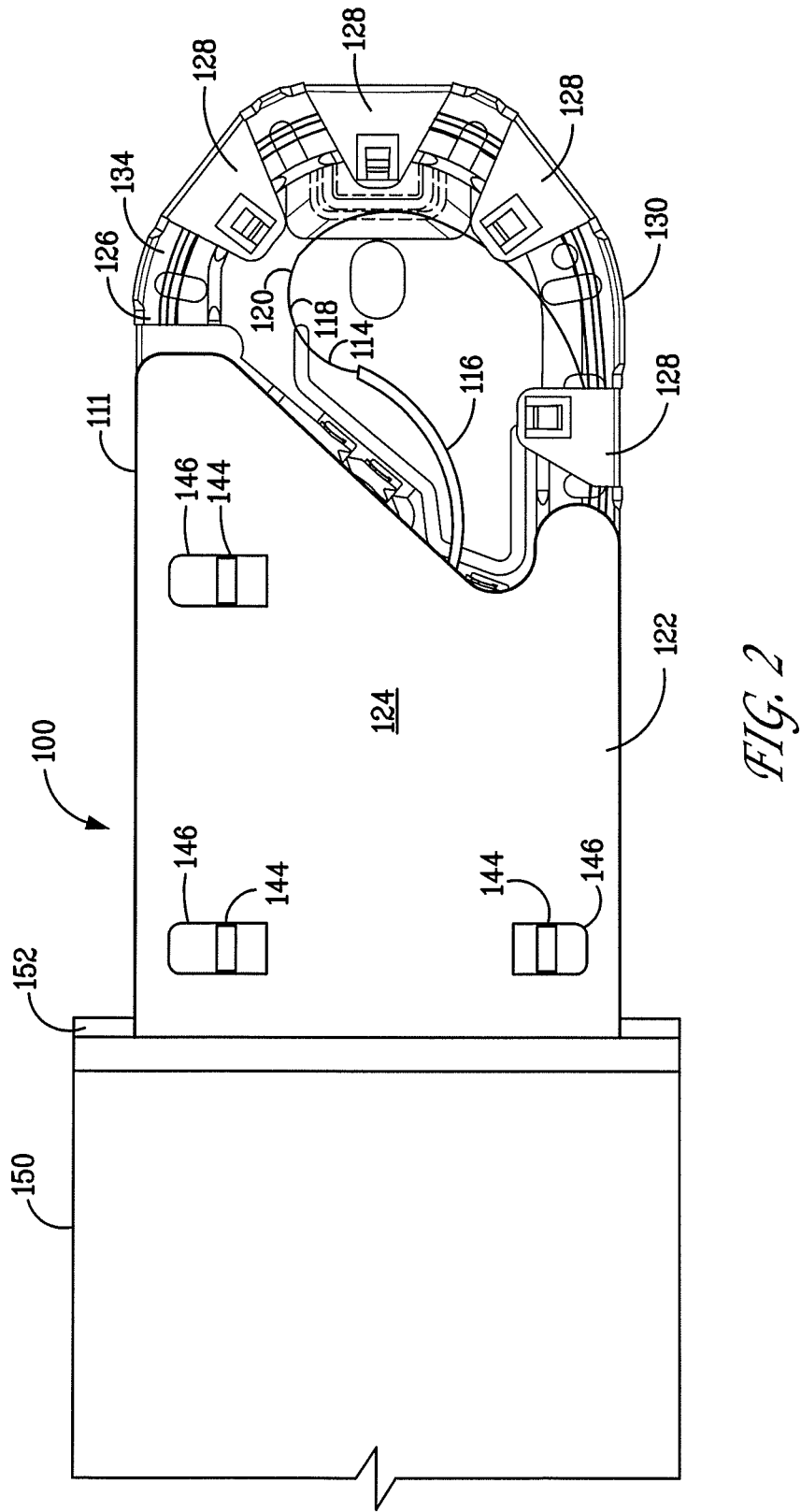
FIG. 2 is a top plan view of another form of a packaged antimicrobial medical device, in accordance herewith, wherein the medical device is a single needle and suture.
Figure 3:
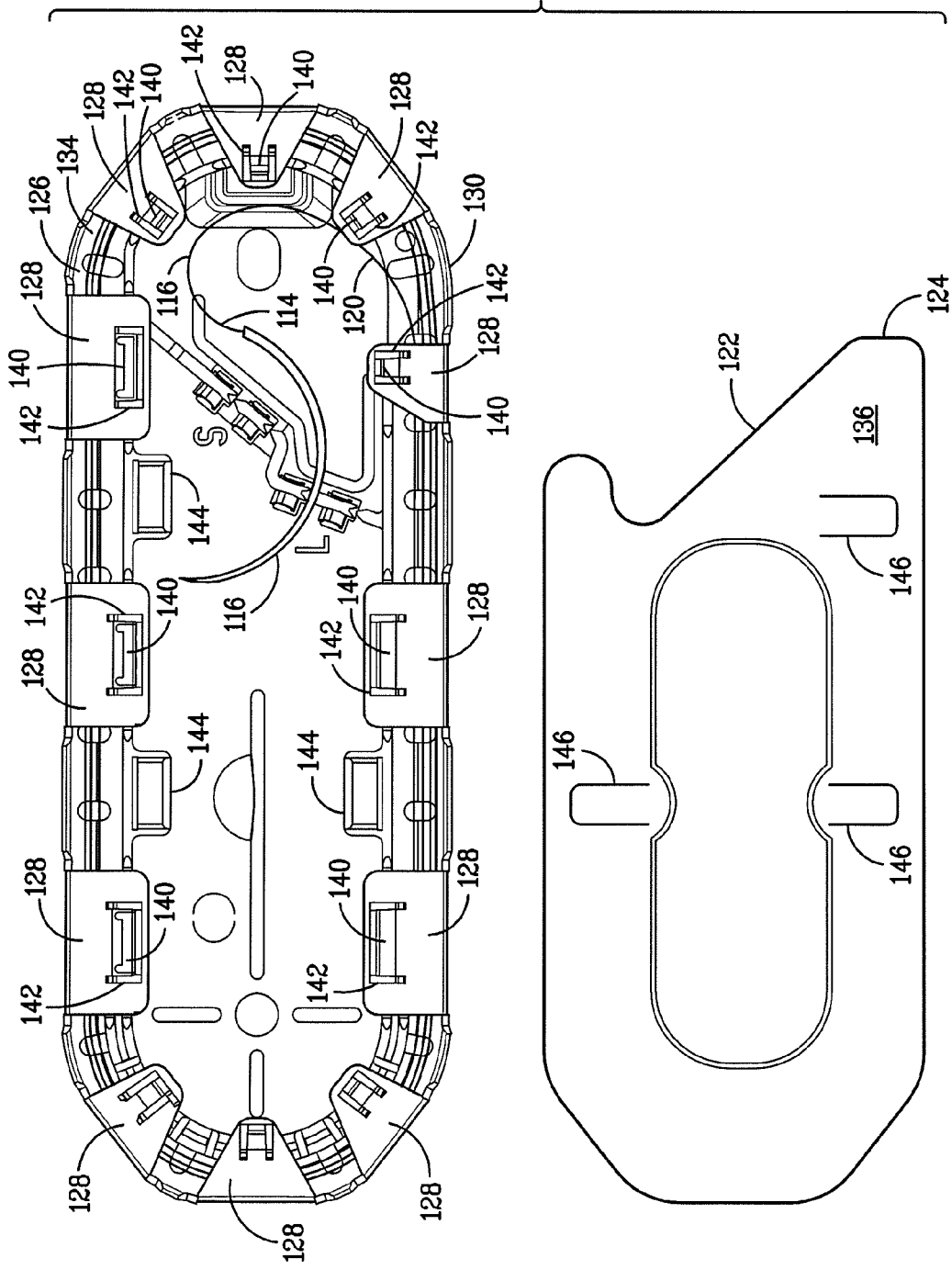
FIG. 3 is a top plan view of the packaged antimicrobial medical device of FIG. 2, wherein the outer cover of the containment compartment has been removed to fully expose the base member.
Figure 4:
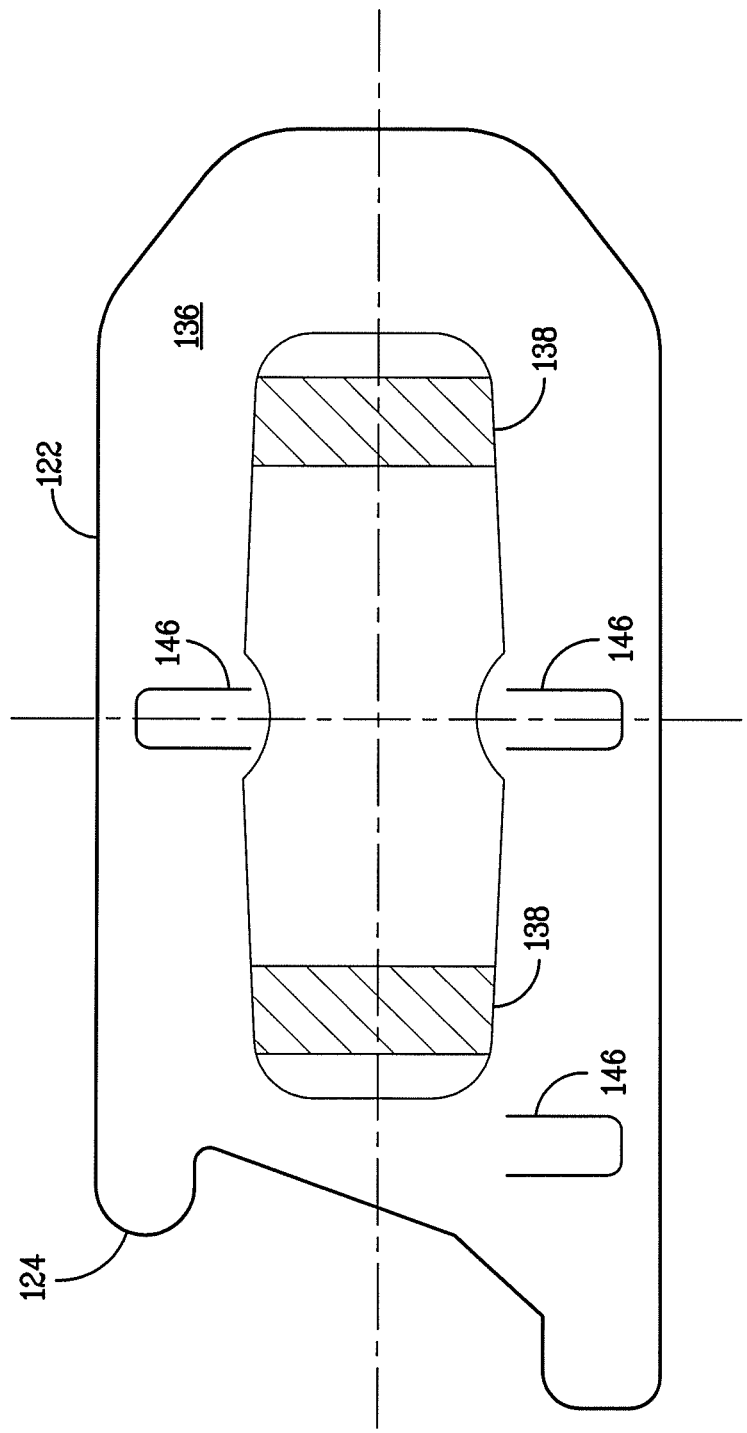
FIG. 4 is a bottom plan view of the outer cover of the containment compartment of the packaged antimicrobial medical device of FIG. 2.
Figure 5:
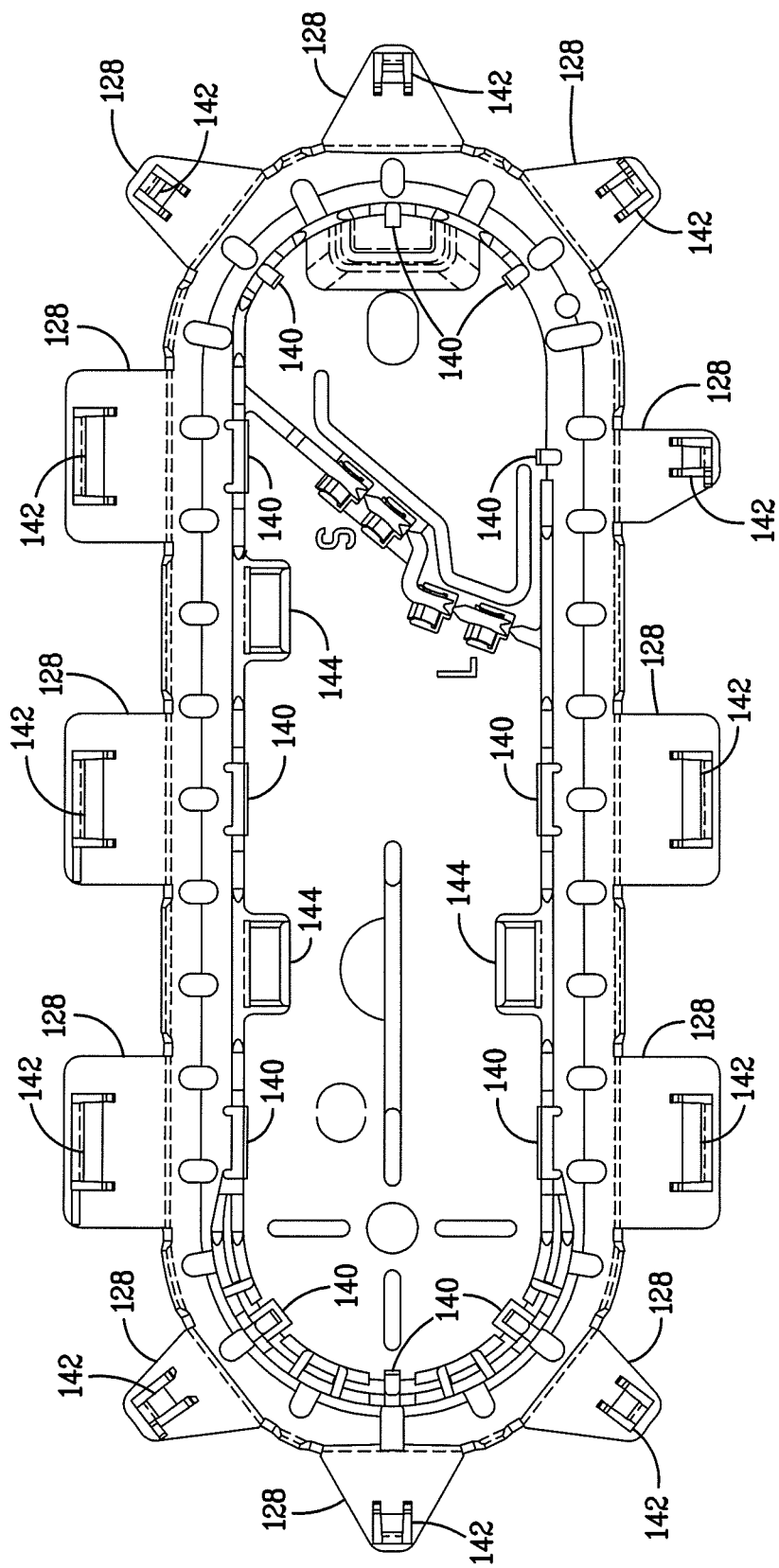
FIG. 5 is a top plan view of the base member of the containment compartment of the packaged antimicrobial medical device of FIG. 2.

Referring in particular to FIGS. 2-4, the packaged antimicrobial medical device 100 of the present invention may be assembled in the following manner. Base member 126 may be provided with a plurality of locking pins 140. Channel cover tab members 128 may be provided with a plurality of locking pin receiving holes 142 for receiving corresponding locking pins 140 upon folding channel cover tab members 128 over locking pins 140. Then, channel cover tab members 128 become affixed to locking pins 140 of base member 126. Advantageously, the use of heating or ultrasonic treatments to firmly affixed channel cover tab members 128 to base member 126 may be avoided. In this embodiment, when containment compartment 112 is so formed, a channel 134 is formed, which may advantageously house a wound suture 118.

In one embodiment, as shown in FIGS. 2-4, outer cover 122 may be provided with a plurality of tabs 146, for positioning within tab receiving members 144, to affix outer cover 122 to base member 126 within outer periphery 130, to at least partially enclose medical device 114.

Further details regarding the construction and geometry of the containment compartments and packages formed therefrom are more fully described in U.S. Pat. Nos. 6,047,815; 6,135,272 and 6,915,623, the contents of each are hereby incorporated by reference in their entirety for all that they disclose.

Containment compartments 12 and 120 may be manufactured from conventional moldable materials. It is especially preferred to use polyolef in materials such as polyethylene and polypropylene, other thermoplastic materials, and polyester materials such as nylon, and equivalents thereof. In one embodiment, the containment compartments 12 and 120 of the present invention may be injection molded, however, they may also be formed by other conventional processes and equivalents thereof, including thermo-forming. If desired, the packages may be manufactured as individual assemblies or components which are then assembled.

Figure 6:
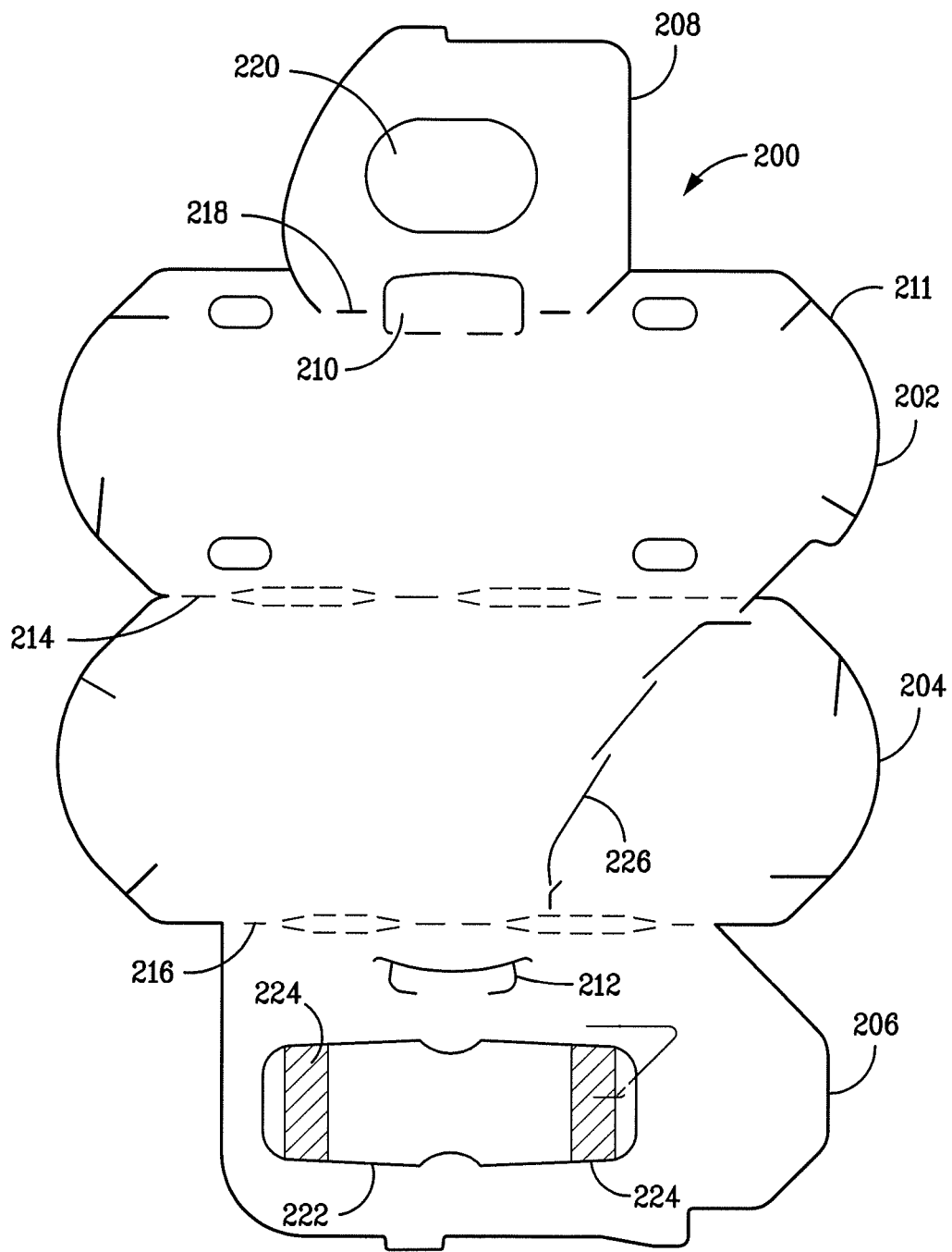
FIG. 6 is a lay flat view of another embodiment of inner package, in the form of a universal folder, in accordance herewith.

Referring now to FIG. 6 another embodiment of a packaged antimicrobial medical device is shown, which includes an inner package 211 having a source of antimicrobial agent. As may be appreciated by those skilled in the art, inner package 211 is in the form of a universal folder and shown in an unfolded, lay-flat form.

As shown, inner package 211 includes a first main outer panel 202, a second main outer panel 204, a first inner panel 206 and a second inner panel 208. To configure inner package 211 to form a universal envelope, the first inner panel 206 is folded inward along fold line 216 and the second inner panel 208 is folded inward along fold line 218. A medical device (not shown), which may be a needle and suture having one or more surfaces, is positioned under the second inner panel 208 of inner package 211 and against the inner surface of second main outer panel 204. First main outer panel 202 may be provided with a tab 210 for mating with a tab receiving means 212, which may be provided within second inner panel 208, as shown. To complete, inner package 211, first main outer panel 202 and second main outer panel 204 are folded along fold line 214 and tab 210 place within tab receiving means 212. As with the other embodiments described herein, one surface may be coated with an adsorbent material to enable the packaged antimicrobial medical device to exhibit improved shelf life over a packaged antimicrobial medical device without such an adsorbent material so provided.

As with the other embodiments described herein, an outer package (not shown) having an inner surface is provided to seal the inner package 211 when positioned within.

The medical devices described herein are generally implantable medical devices and implants, including but not limited to mono and multifilament sutures, surgical meshes such as hernia repair mesh, hernia plugs, brachy seed spacers, suture clips, suture anchors, adhesion prevention meshes and films, and suture knot clips. Also included are implantable medical devices that are absorbable and non-absorbable.

An absorbable polymer is defined herein as a polymer that will degrade and be absorbed by the body over a period of time when exposed to physiological conditions. Absorbable medical devices typically are formed from generally known, conventional absorbable polymers including but not limited to glycolide, lactide, copolymers of glycolide, or mixtures of polymers, such as polydioxanone, polycaprolactone, oxidized regenerated cellulose and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Preferably, absorbable medical devices are made from polydioxanone, poliglecaprone, or a glycolide/lactide copolymer. Examples of absorbable medical device include mono and multifilament sutures. The multifilament suture includes sutures wherein a plurality of filaments is formed into a braided structure. Examples of non-absorbable medical devices include mono and multifilament sutures, surgical meshes such as hernia repair mesh, hernia plugs and brachy seed spacers, which may be polymeric or nonpolymeric. Non-absorbable medical devices may be made in whole or in part from polymeric materials that include, but are not limited to, polyolefins such as polypropylene; polyamides such as nylon; chlorinated and/or fluorinated hydrocarbons such as Teflon® material; or polyesters such as Dacron® synthetic polyesters; or from nonpolymeric materials that include, but are not limited to, silks, collagen, stainless steel, titanium, cobalt chromium alloy, nitinol. Preferably, the non-absorbable medical devices are made from nylon or polypropylene.

In one embodiment, the sutures and needles that can be packaged in the packages disclosed herein include conventional surgical needles and conventional bioabsorbable and nonabsorbable surgical sutures and equivalents thereof. The packages of the present invention are useful to package small diameter sutures which were previously difficult to package in tray packages because of removal or hang-up problems upon withdrawal of such suture from the packages.

Suitable antimicrobial agents may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, as described in U.S. Pat. No. 3,629,477, and represented by the following formula:

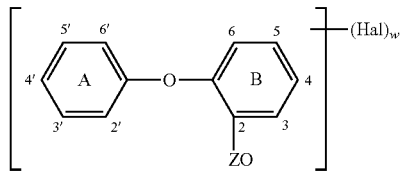

In the above formula, each Hal represents identical or different halogen atoms, Z represents hydrogen or an acyl group, and w represents a positive whole number ranging from 1 to 5, and each of the benzene rings, but preferably ring A can also contain one or several lower alkyl groups which may be halogenated, a lower alkoxy group, the allyl group, the cyano group, the amino group, or lower alkanoyl group. Preferably, methyl or methoxy groups are among the useful lower alkyl and lower alkoxy groups, respectively, as substituents in the benzene rings. A halogenated lower alkyl group, trifluoromethyl group is preferred.

Antimicrobial activity similar to that of the halogen-o-hydroxydiphenyl ethers of the above formula is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxydiphenyl ether, commonly referred to as triclosan (manufactured by Ciba Geigy under the trade name Irgasan DP300 or Irgacare MP). Triclosan is a white powdered solid with a slight aromatic/phenolic odor. As may be appreciated, it is a chlorinated aromatic compound which has functional groups representative of both ethers and phenols.

Triclosan is a broad-spectrum antimicrobial agent that has been used in a variety of products, and is effective against a number of organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

In addition to the antimicrobial agents described above, the medical device optionally may have a biocide, a disinfectant and/or an antiseptic, including but not limited to alcohols such as ethanol and isopropanol; aldehydes such as glutaraldehyde and formaldehyde; anilides such as triclorocarbanilide; biguanides such as chlorhexidine; chlorine-releasing agents such as sodium hypochlorite, chlorine dioxide and acidified sodium chlorite; iodine-releasing agents such as povidone-iodine and poloxamer-iodine; metals such as silver nitrate, silver sulfadiazine, other silver agents, copper-8-quinolate and bismuth thiols; peroxygen compounds such as hydrogen peroxide and peracetic acid; phenols; quaternary ammonium compounds such as benzalkonium chloride, cetrimide and ionenes-polyquaternary ammonium compounds. The medical device optionally may have antibiotics, including but not limited to penicillins such as amoxicillin, oxacillin and piperacillin; cephalosporins parenteral such as cefazolin, cefadroxil, cefoxitin, cefprozil, cefotaxime and cefdinir; monobactams such as aztreonam; beta-lactamase inhibitors such as clavulanic acid sulbactam; glycopeptide such as vancomycin; polymixin; quinolones such as nalidixic acid, ciprofloxacin and levaquin; metranidazole; novobiocin; actinomycin; rifampin; aminoglycosides such as neomycin and gentamicin; tetracyclines such as doxycycline; chloramphenicol; macrolide such as erythromycin; clindamycin; sulfonamide such as sulfadiazine; trimethoprim; topical antibiotics; bacitracin; gramicidin; mupirocin; and/or fusidic acid. Optionally, the medical device may have antimicrobial peptides such as defensins, magainin and nisin; lytic bacteriophage; surfactants; adhesion blockers such as antibodies, oligosaccharides and glycolipids; oligonucleotides such as antisense RNA; efflux pump inhibitors; photosensitive dyes such as porphyrins; immune modulators such as growth factors, interleukins, interferons and synthetic antigens; and/or chelators such as EDTA, sodium hexametaphosphate, lactoferrin and transferrin.

The antimicrobial agent may be delivered to the medical device from an antimicrobial agent source that is positioned within or attached to the inner surface of a package. Specifically, the antimicrobial agent is transferred from the antimicrobial agent source to the medical device when the package, the antimicrobial agent source and the medical device are subjected to time, temperature and pressure conditions, as described below. For example, the antimicrobial agent source may be an antimicrobial agent-loaded paper reservoir, an antimicrobial agent-loaded porous pouch reservoir, an antimicrobial agent-loaded plastic reservoir, an antimicrobial agent-loaded sponge or foam reservoir, an antimicrobial agent-loaded tape (see element, or an antimicrobial agent-loaded tablet. Alternatively, the antimicrobial agent source may be integral with the package itself, i.e., antimicrobial agent incorporated into or on the package itself, such as but not limited to, applied directly on the inner surface of the package. Where the antimicrobial agent source is in a paper or plastic reservoir, such reservoir may be integral with one or more packaging component in the package.

As indicated, the packaged antimicrobial medical devices disclosed herein utilize an adsorbent material to improve shelf life over packaged antimicrobial sutures that do not utilize an adsorbent material. It has been shown that the shelf life of an antimicrobial medical device, such as a triclosan-containing suture, is believed to be limited by triclosan levels that increase over time during normal and accelerated storage conditions. It has been surprisingly discovered that certain adsorbent materials may serve as a buffering agent to moderate the rate of increase of triclosan on the medical device.

Referring again to FIGS. 1, 2 and 6, in one embodiment, the adsorbent material is provided by coating the adsorbent material on at least a portion of one surface of the inner package, 11, 111 or 211. In another embodiment, the adsorbent material is provided by placing an adsorbent substrate (not shown) within the outer package. In another embodiment, the adsorbent substrate is formed by coating a substrate with an adsorbent material. In yet another embodiment, the adsorbent substrate is formed of an adsorbent material. In still yet another embodiment, the adsorbent material provided on at least a portion of one surface of the inner package, is provided on at least one surface of outer cover 22 or 122.

Adsorbent materials having utility in the practice of the present invention include any material having adsorbent properties, including bentonite, activated carbon, activated alumina, silica gel, zeolite, super-absorbant polymers, humectants, polymeric coatings, ground polymeric coatings, natural products, non-paper substrates, and clays, including kaolin. Clays, such as kaolin, have proven to be particularly effective.

Referring to FIG. 6, inner package 211 comprises a universal envelope formed from a paperboard stock having at least one surface coated with an adsorbent material. A suitable paperboard stock having utility in the practice of the inventions disclosed herein is Invercote T2®, available from Iggesund Paperboard of Edison, N.J.

Additionally, the medical device may optionally have a coating thereon, and/or may optionally comprise one or more surfaces having an antimicrobial agent disposed thereon prior to any transfer of antimicrobial agent to the medical device from the antimicrobial agent source. For example, it is advantageous to apply a coating composition having an antimicrobial agent therein to the surface of the medical device. Examples of medical devices, as well as coatings that may be applied thereto, may be found in U.S. Pat. Nos. 4,201,216, 4,027,676, 4,105,034, 4,126,221, 4,185,637, 3,839,297, 6,260,699, 5,230,424, 5,555,976, 5,868,244, and 5,972,008, each of which is hereby incorporated herein in its entirety. As disclosed in U.S. Pat. No. 4,201,216, the coating composition may include a film-forming polymer and a substantially water-insoluble salt of a $C_6$ or higher fatty acid. As another example, an absorbable coating composition that may be used for an absorbable medical device may include poly(alkylene oxylates) wherein the alkylene moieties are derived from $C_6$ or mixtures of $C_4$ to $C_{12}$ diols, which is applied to a medical device from a solvent solution, as disclosed in U.S. Pat. No. 4,105,034. The coating compositions may include a polymer or copolymer, which may include lactide and glycolide, as a binding agent. The coating compositions may also include calcium stearate, as a lubricant; and an antimicrobial agent. The coating may be applied to the device by solvent-based coating techniques, such as dip coating, spray coating, or suspended drop coating, or any other coating means.

Absorbable medical devices are moisture sensitive, that is, they are devices that will degrade if exposed to moisture in the atmosphere or in the body. It is known by those of ordinary skill in the art that medical devices made from absorbable polymers may deteriorate and lose their strength if they come into contact with water vapor prior to use during surgery. For instance, the desirable property of in vivo tensile strength retention for sutures will be rapidly lost if the sutures are exposed to moisture for any significant period of time prior to use. Therefore, it is desirable to use a hermetically sealed package for absorbable medical devices. A hermetically sealed package is defined herein to mean a package made of a material that serves as both a sterile barrier and a gas barrier, i.e., prevents or substantially inhibits moisture and gas permeation.

Referring again to FIGS. 1 and 2, materials useful for constructing outer packages 50 and 150 and the outer package for use with universal envelopes, may include, for example, include single and multilayered conventional metal foil products, often referred to as heat-sealable foils. These types of foil products are disclosed in U.S. Pat. No. 3,815,315, which is hereby incorporated by reference in its entirety. Another type of foil product that may be utilized is a foil laminate referred to in the field of art as a peelable foil. Examples of such peelable foil and substrates are disclosed in U.S. Pat. No. 5,623,810, which is hereby incorporated by reference in its entirety. If desired, conventional non-metallic polymer films in addition to or in lieu of metal foil may be used to form the package for absorbable medical devices. Such films are polymeric and may include conventional polyolefins, polyesters, acrylics, halogenated hydrocarbons and the like, combinations thereof and laminates. These polymeric films substantially inhibit moisture and oxygen permeation and may be coated with conventional coatings, such as, for example, mineral and mineral oxide coatings that decrease or reduce gas intrusion. The package may comprise a combination of polymer and metal foils, particularly a multi-layer polymer/metal-foil composite, such as a polyester/aluminum foil/ethylacrylic acid laminate.

Nonabsorbable medical devices may be packaged in any of the materials described above. In addition, it is desirable to package nonabsorbable medical devices in a package made of a material that serves as a sterile barrier, such as a porous material, i.e., medical grade paper, or a polymeric film or fabric that is permeable to moisture and gas, i.e., Tyvek® nonwoven material, manufactured by E. I. du Pont de Nemours and Company of Wilmington, Del., and made from high-density polyethylene fibers. Preferably, nonabsorbable medical devices are packaged in the same packaging materials that are used for absorbable medical devices, such as hermetically sealed packages, when it is desirable to have antimicrobial medical devices having a shelf life of at least 6 months, preferably at least 1 year and most preferably at least 2 years.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. An efficacious antimicrobial agent against *Staphylococcus* is 2,4,4'-trichloro-2'-hydroxy-diphenyl ether. This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrases "an amount sufficient to substantially inhibit bacterial colonization" and "an effective amount" of the antimicrobial agent, as used herein, are defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the antimicrobial agent diffuses through the medium, and as long as the concentration of the antimicrobial agent is above the minimum inhibitory concentration (MIC), none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

In accordance with various methods of the present invention, method of making a packaged antimicrobial suture having improved shelf life. Is provided. The method includes the steps of providing an inner package having a source of antimicrobial agent, providing an adsorbent material effective to adsorb a portion of the antimicrobial agent over time, positioning a suture within the inner package, the suture comprising one or more surfaces, covering the inner package with an outer package having an inner surface and subjecting the suture, the inner package and the inner surface of the outer package to time, temperature and pressure conditions sufficient to vapor transfer an effective amount of the antimicrobial agent from the antimicrobial agent source to the suture and the inner package, thereby substantially inhibiting bacterial colonization on the suture and the inner package. Advantageously, the packaged antimicrobial suture so produced exhibit improved shelf life over a packaged antimicrobial suture without an adsorbent material so provided.

As will be described in more detail hereinbelow, the step of subjecting the suture, the inner package and the inner surface of the outer package to conditions sufficient to vapor transfer an effective amount of the antimicrobial agent includes the steps of placing the outer package having the inner package and the suture therein in a sterilization unit, heating the sterilization unit to a first temperature, adjusting the pressure in the sterilization unit to a first pressure value, injecting steam into the sterilization unit to expose the inner surface of the outer package, the inner package and the suture to water vapor for a first period of time, adjusting the pressure within the sterilization unit to a second pressure value, introducing a chemical sterilization agent into the sterilization unit, maintaining the chemical sterilization agent in the sterilization unit for a second period of time to render a sufficient amount of microorganisms non-viable, removing residual moisture and chemical sterilization agent from the suture and drying the packaged antimicrobial suture to a desired moisture level. In one embodiment, the step of introducing a chemical sterilization agent comprises introducing ethylene oxide gas into the sterilization unit.

In one embodiment, the medical device is directly exposed to the antimicrobial agent, i.e., the antimicrobial agent source is located in the package having the medical device. For example, the package may contain an antimicrobial agent source, may have an antimicrobial agent source attached to the inner surface of the package, or the antimicrobial agent source may be integral with one or more packaging component in the package or with the package itself. In these embodiments, the medical device is positioned within the package and may initially be free of an antimicrobial agent or may initially comprise one or more surfaces having an antimicrobial agent disposed thereon. As indicated, the package, the antimicrobial agent source and the medical device are then subjected to time, temperature and pressure conditions sufficient to vapor transfer an effective amount of the antimicrobial agent from the antimicrobial agent source to the medical device, thereby substantially inhibiting bacterial colonization on the medical device.

In the case where the medical device is initially free of an antimicrobial agent, the antimicrobial agent is delivered to the medical device from an antimicrobial agent source when the package, the antimicrobial agent source and the medical device are subjected to time, temperature and pressure conditions sufficient to vapor transfer a portion of the antimicrobial agent from the antimicrobial agent source to the medical device.

In the case where the medical device initially comprises one or more surfaces having an antimicrobial agent disposed thereon, the time, temperature and pressure conditions are sufficient to vapor transfer a portion of each of the antimicrobial agent disposed on the medical device and the antimicrobial agent in the antimicrobial agent source to the inner surface of the package, such that an effective amount of the antimicrobial agent is retained on the medical device, thereby substantially inhibiting bacterial colonization on the medical device and the inner surface of the package. In this embodiment, the amount or concentration of antimicrobial agent on the medical device is stabilized by providing additional antimicrobial agent in the packaging environment.

Alternatively, the medical device may be positioned within a package, and the package having the medical device is exposed indirectly to an external antimicrobial agent source, i.e., the antimicrobial agent source is external to the package having the medical device. Specifically, the antimicrobial agent source and the package having the medical device are subjected to time, temperature and pressure conditions sufficient to vapor transfer an effective amount of the antimicrobial agent from the antimicrobial agent source to the medical device within the package, thereby substantially inhibiting bacterial colonization on the medical device. In this embodiment, the package may be made from a material that serves as a sterile barrier, such as a porous material or polymeric film that is permeable to moisture and gas, such that a gaseous antimicrobial agent source is capable of permeating or transmitting as a vapor through the package. For example, the package having the medical device may be placed in a sealed environment, and the antimicrobial agent source may be contained within the sealed environment or may be subsequently introduced to the sealed environment. The antimicrobial agent source may be any vapor form of the antimicrobial agent.

The rate of vapor transfer of an antimicrobial agent such as triclosan from the antimicrobial agent source to the medical device is substantially dependent upon the time, temperature and pressure conditions under which the package and the medical device are processed, stored and handled. The conditions to effectively vapor transfer an antimicrobial agent such as triclosan include a closed environment, atmospheric pressure, a temperature of greater than 40° C., for a period of time ranging from 4 to 8 hours. Also included are any combinations of pressure and temperature to render a partial pressure for the antimicrobial agent that is the same as or greater than the partial pressure rendered under the conditions described above, in combination with a period of time sufficient to render an effective amount or concentration of the antimicrobial agent on the medical device, i.e., the minimum inhibitory concentration (MIC) for S. aureus or greater. Specifically, it is known to one of ordinary skill that if the pressure is reduced, the temperature may be reduced to effect the same partial pressure. Alternatively, if the pressure is reduced, and the temperature is held constant, the time required to render an effective amount or concentration of the antimicrobial agent on the medical device may be shortened. Generally, the amount of antimicrobial agent in the antimicrobial agent source is at least that amount which is necessary to deliver the effective amount of the antimicrobial agent on the medical device, when exposed to the conditions described below.

Medical devices typically are sterilized to render microorganisms located thereon substantially non-viable. In particular, sterile is understood in the field of art to mean a minimum sterility assurance level of $10^{-6}$. Examples of sterilization processes are described in U.S. Pat. Nos. 3,815,315, 3,068,864, 3,767,362, 5,464,580, 5,128,101 and 5,868,244, each of which is incorporated herein in its entirety. Specifically, absorbable medical devices may be sensitive to radiation and heat. Accordingly, it may be desirable to sterilize such devices using conventional sterilant gases or agents, such as, for example, ethylene oxide gas.

An ethylene oxide sterilization process is described below, since the time, temperature and pressure conditions sufficient to vapor transfer the antimicrobial agent from the antimicrobial agent source to the medical device, are present in an ethylene oxide sterilization process. However the time, temperature and pressure conditions sufficient to vapor transfer the antimicrobial agent from the antimicrobial agent source to the medical device, may be effected alone or in other types of sterilization processes, and are not limited to an ethylene oxide sterilization process or to sterilization processes in general.

As discussed above, absorbable medical devices are sensitive to moisture and are therefore often packaged in hermetically sealed packages, such as sealed foil packages. However, sealed foil packages are also impervious to sterilant gas. In order to compensate for this and utilize foil packages in ethylene oxide gas sterilization processes, processes have been developed using foil packages having gas permeable or pervious vents (e.g., Tyvek® nonwoven material, manufactured by E. I. du Pont de Nemours and Company of Wilmington, Del.). The gas permeable vents are mounted to an open end of the package and allow the passage of air, water vapor and ethylene oxide into the interior of the package. After the sterilization process is complete, the package is sealed adjacent to the vent so the vent is effectively excluded from the sealed package, and the vent is cut away or otherwise removed, thereby producing a gas impervious hermetically sealed package. Another type of foil package having a vent is a pouch-type package having a vent mounted adjacent to an end of the package, wherein the vent is sealed to one side of the package creating a vented section. After the sterilization process is complete the package is sealed adjacent to the vented section, and the sealed package is cut away for the vented section.

In one embodiment, the antimicrobial agent source is placed within the package, attached to the inner surface of the package, or is integral with one or more packaging component in the package or with the package itself. After the peripheral seal and side seals have been formed in the package, the packaged medical device may be placed into a conventional ethylene oxide sterilization unit. If the package is a foil package, the antimicrobial agent source may be any of the antimicrobial agent sources described above or the antimicrobial agent source may be an antimicrobial agent loaded-gas permeable vent. For example, an antimicrobial agent such as triclosan may be loaded onto a Tyvek® gas permeable vent by coating the Tyvek® strip with a solution of ethyl acetate and triclosan; the antimicrobial agent loaded gas permeable vent is positioned within a package by mounting it to a hermetic packaging material; the medical device is positioned within the hermetic packaging material; the periphery of the hermetic packaging material is sealed in a manner to enclose the medical device and to allow the passage of gas into the interior of the hermetic packaging material through the vent; the packaging material having the antimicrobial agent loaded gas permeable vent and the medical device is subjected to time, temperature and pressure conditions sufficient to vapor transfer an effective amount of the antimicrobial agent from the antimicrobial agent loaded gas permeable vent to the medical device; the packaging material is sealed to enclose the medical device and exclude the vent; and the vent is cut away to thereby produce an antimicrobial medical device.

In another embodiment, the antimicrobial agent source may be introduced into the sterilization or other unit external to the package having the medical device. For example, the medical device is positioned within the package; the package having the medical device is exposed to an antimicrobial agent source; and the package having the medical device and the antimicrobial agent source is subjected to time, temperature and pressure conditions sufficient to vapor transfer an effective amount of the antimicrobial agent from the antimicrobial agent source to the medical device within the package, thereby substantially inhibiting bacterial colonization on the medical device. The package may be made from a material that serves as a sterile barrier, such as a porous material or a polymeric film that is permeable to moisture and gas, or from a material that results in a hermetically sealed package.

Prior to the start of the cycle, the sterilization unit may be heated to an internal temperature of about 25° C. The sterilization unit is maintained about 22 to 37° C. throughout the humidification and sterilization cycles. Next, a vacuum may be drawn on the sterilization unit to achieve a vacuum of approximately 1.8 to 6.0 kPa. In a humidification cycle, steam then may be injected to provide a source of water vapor for the product to be sterilized. The packaged medical devices may be exposed to water vapor in the sterilization unit for a period of time of about 60 to 90 minutes. Times may vary, however, depending upon the medical device being sterilized.

Following this humidification portion of the cycle, the sterilization unit may be pressurized by the introduction of dry inert gas, such as nitrogen gas, to a pressure of between about 42 and 48 kPa. Once the desired pressure is reached, pure ethylene oxide may be introduced into the sterilization unit until the pressure reaches about 95 kPa. The ethylene oxide may be maintained for a period of time effective to sterilize the packaged medical device. For example, the ethylene oxide may be maintained in the sterilization unit for about 360 to about 600 minutes for surgical sutures. The time required to sterilize other medical devices may vary depending upon the type of product and the packaging. The ethylene oxide then may be evacuated from the sterilization unit and the unit may be maintained under vacuum at a pressure of approximately 0.07 kPa for approximately 150 to 300 minutes in order to remove residual moisture and ethylene oxide from the sterilized packaged medical devices. The pressure in the sterilization unit may be returned to atmospheric pressure.

The following stage of the process is a drying cycle. The packaged medical device may be dried by exposure to dry nitrogen and vacuum over a number of cycles sufficient to effectively remove residual moisture and water vapor from the packaged medical device to a preselected level. During these cycles, the packaged medical device may be subjected to a number of pressure increases and decreases, at temperatures greater than room temperature. Specifically, the jacket temperature of the drying chamber may be maintained at a temperature of between approximately 53° C. to 57° C. throughout the drying cycle. Higher temperatures, however, may be employed, such as about 65° C. to 70° C. for sutures, and higher depending upon the medical device being sterilized. A typical drying cycle includes the steps of increasing the pressure with nitrogen to approximately 100 kPa, evacuating the chamber to a pressure of approximately 0.07 kPa over a period of 180 to 240 minutes, reintroducing nitrogen to a pressure of 100 kPa and circulating the nitrogen for approximately 90 minutes, evacuating the chamber to a pressure of approximately 0.01 kPa over a period of approximately 240 to 360 minutes and maintaining a pressure of not more than 0.005 kPa for an additional 4 to 96 hours. At the end of the humidification, sterilization and drying cycles, which takes typically about 24 hours, the vessel is returned to ambient pressure with dry nitrogen gas. Once drying to the preselected moisture level is complete, the packaged medical device may be removed from the drying chamber and stored in a humidity controlled storage area.

Upon completion of the sterilization process, the antimicrobial medical device, the package and/or the packaging component have thereon an amount of the antimicrobial agent effective to substantially inhibit colonization of bacteria on or adjacent the antimicrobial device, the package and/or the packaging component.

As indicated above, it has been shown that the shelf life of an antimicrobial medical device, such as a triclosan-containing suture, can be limited by increasing levels of triclosan that occur during normal and accelerated storage conditions. In some case, shelf life is limited to a period not to exceed two years, due to the impact of this phenomenon. The packaged antimicrobial medical devices disclosed herein utilize an adsorbent material to improve shelf life over packaged antimicrobial sutures that do not utilize an adsorbent material. In accordance with the methods disclosed herein, in one embodiment, the method of making a packaged antimicrobial device includes the step of coating the adsorbent material on at least a portion of one surface of the inner package. In another embodiment, the adsorbent material is provided by placing an adsorbent substrate within the outer package. In still another embodiment, the adsorbent substrate is formed by coating a substrate with an adsorbent material. In a still further embodiment, the adsorbent substrate is formed of an adsorbent material. In a yet still further embodiment, the inner package comprises a universal envelope formed from a paperboard stock having at least one surface coated with an adsorbent material.

Adsorbent materials having utility in the practice of the present invention include any material having adsorbent properties, including bentonite, activated carbon, activated alumina, silica gel, zeolite, super-absorbent polymers, humectants, polymeric coatings, ground polymeric coatings, natural products, non-paper substrates, and clays, including kaolin. Clays, such as kaolin, have proven to be particularly effective.

In one embodiment, a method of increasing the shelf life of a packaged antimicrobial medical device is provided. The method includes the steps of providing an inner package having a source of antimicrobial agent, providing an adsorbent material effective to adsorb a portion of the antimicrobial agent over time, positioning a medical device within the inner package, the medical device comprising one or more surfaces, covering the inner package with an outer package having an inner surface and subjecting the medical device, the inner package and the inner surface of the outer package to time, temperature and pressure conditions sufficient to vapor transfer an effective amount of the antimicrobial agent from the antimicrobial agent source to the medical device and the inner package, thereby substantially inhibiting bacterial colonization on the medical device and the inner package. The packaged antimicrobial medical device exhibits improved shelf life over a packaged antimicrobial medical device without an adsorbent material so provided.

The invention will now be more particularly described with reference to the following non-limiting Examples.

EXAMPLES

A series of stability studies was run using PDS Plus® sutures (a monofilament polydioxanone suture that is commercially available from Ethicon, Inc.), packaged in universal folders and relay trays. Studies were conducted on size 1 and size 3/0 sutures. For each suture size/package configuration, samples were fabricated using uncoated paper stock, obtained from Monadnock Paper Mills, Inc., of Bennington, N.H., and clay-coated paper stock (Invercote T2®, available from Iggesund Paperboard of Edison, N.J.). The study designations are shown below:

VAP2005-003 PDS Plus®—Universal Folder—Uncoated Paper
VAP2007-058 PDS Plus®—Universal Folder—Coated Paper
VAP2005-003 PDS Plus®—Relay Tray—Uncoated Paper
VAP2007-054 PDS Plus®—Relay Tray—Coated Paper For each study the finished product was stored at 50° C. for up to 5 months and at 25° C. for up to 24 months. At the designated time period samples were tested for triclosan content in the suture and compared to the starting values. Multiple triclosan dispense levels were used for each test condition.

Example 1

PDS Plus Size 1 in Universal Folder Stored at 25° C.

Stability studies were run using size 1 PDS Plus® sutures, packaged in universal folders. For each study the finished product was stored at 25° C. for up to 24 months. Samples were tested for triclosan content in the suture and compared to the starting values. Results for these studies are presented below and graphically depicted in FIG. 7.

| | | VAP2005-003 - Uncoated Paper | | | | | VAP2007-058 - Coated Paper | | | | |
|---|---|---|---|---|---|---|---|---|---|---|---|
| | | Triclosan (ppm) | | Percent Increase | | | Triclosan (ppm) | | Percent Increase | | |
| | | | | | | | 2.5 mg (1) | 3.6 mg (1) | 2.5 mg (1) | 3.6 mg (1) | |
| Size | Storage Time (Months) | 2 mg Triclosan Dispense Amount | 4 mg Triclosan Dispense Amount | 2 mg Triclosan Dispense Amount | 4 mg Triclosan Dispense Amount | Ave UF Increase (%) | 4.2 mg (3/0) Triclosan Dispense Amount | 4.66 mg (3/0) Triclosan Dispense Amount | 4.2 mg (3/0) Triclosan Dispense Amount | 4.66 mg (3/0) Triclosan Dispense Amount | Ave UF Increase (%) |
| 1 | 0 | 2083 | 3491 | 0.0% | 0.0% | 0.0% | 1559 | 2314 | 0.0% | 0.0% | 0.0% |
| 1 | 1 | 2313 | 2860 | 11.0% | −18.1% | −3.5% | 1559 | 2198 | 0.0% | −5.0% | −2.5% |
| 1 | 3 | 2582 | 3580 | 24.0% | 2.5% | 13.3% | 1648 | 2275 | 5.7% | −1.7% | 2.0% |
| 1 | 5 | 2802 | 3738 | 34.5% | 7.1% | 20.8% | 1623 | 2241 | 4.1% | −3.1% | 0.5% |
| 1 | 7 | | | | | | 1784 | 2361 | 14.4% | 2.0% | 8.2% |
| 1 | 9 | 2997 | 5662 | 43.9% | 62.2% | 53.0% | 1689 | 2475 | 8.3% | 7.0% | 7.7% |
| 1 | 12 | 3672 | 5659 | 76.3% | 62.1% | 69.2% | 1881 | 2383 | 20.7% | 3.0% | 11.8% |
| 1 | 15 | | | | | | 1800 | 2511 | 15.5% | 8.5% | 12.0% |
| 1 | 18 | 4812 | 7456 | 131.0% | 113.6% | 122.3% | | | | | |
| 1 | 24 | 5321 | 8216 | 155.4% | 135.3% | 145.4% | | | | | |

Example 2

PDS Plus Size 3/0 in Universal Folder Stored at 25° C.

Stability studies were run using size 3/0 PDS Plus® sutures, packaged in universal folders. For each study the finished product was stored at 25° C. for up to 24 months. Samples were tested for triclosan content in the suture and compared to the starting values. Results for these studies are presented below and graphically depicted in FIG. 8.

| | | VAP2005-003 - Uncoated Paper | | | | | VAP2007-058 - Coated Paper | | | | |
|---|---|---|---|---|---|---|---|---|---|---|---|
| | | Triclosan (ppm) | | Percent Increase | | | Triclosan (ppm) | | Percent Increase | | |
| | | | | | | | 2.5 mg (1) | 3.6 mg (1) | 2.5 mg (1) | 3.6 mg (1) | |
| Size | Storage Time (Months) | 2 mg Triclosan Dispense Amount | 4 mg Triclosan Dispense Amount | 2 mg Triclosan Dispense Amount | 4 mg Triclosan Dispense Amount | Ave UF Increase (%) | 4.2 mg (3/0) Triclosan Dispense Amount | 4.66 mg (3/0) Triclosan Dispense Amount | 4.2 mg (3/0) Triclosan Dispense Amount | 4.66 mg (3/0) Triclosan Dispense Amount | Ave UF Increase (%) |
| 3/0 | 1 | 5078 | 8761 | −10.3% | 33.2% | 11.5% | 5478 | 5698 | 4.6% | 1.9% | 3.3% |
| 3/0 | 3 | 5958 | 8357 | 5.2% | 27.1% | 16.2% | 5609 | 6081 | 7.1% | 8.8% | 7.9% |
| 3/0 | 5 | 6284 | 10508 | 11.0% | 59.8% | 35.4% | 5611 | 5918 | 7.2% | 5.9% | 6.5% |
| 3/0 | 7 | | | | | | 5702 | 6367 | 8.9% | 13.9% | 11.4% |
| 3/0 | 9 | 7802 | 14702 | 37.8% | 123.5% | 80.7% | 5940 | 6214 | 13.4% | 11.2% | 12.3% |
| 3/0 | 12 | 7883 | 14357 | 39.3% | 118.3% | 78.8% | 6268 | 6872 | 19.7% | 22.9% | 21.3% |
| 3/0 | 15 | | | | | | 5587 | 6615 | 6.7% | 18.3% | 12.5% |
| 3/0 | 18 | 9010 | 16207 | 59.2% | 146.4% | 102.8% | | | | | |
| 3/0 | 24 | 10412 | 18501 | 83.9% | 181.3% | 132.6% | | | | | |

Example 3

PDS Plus Size 1 in Universal Folder Stored at 50° C.

Stability studies were run using size 1 PDS Plus® sutures, packaged in universal folders. For each study the finished product was stored at 50° C. for up to 5 months. Samples were tested for triclosan content in the suture and compared to the starting values. Results for these studies are presented below and graphically depicted in FIG. 9.

| | | VAP2005-003 - Uncoated Paper | | | | | VAP2007-058 - Coated Paper | | | | |
|---|---|---|---|---|---|---|---|---|---|---|---|
| | | Triclosan (ppm) | | Percent Increase | | | Triclosan (ppm) | | Percent Increase | | |
| | | | | | | | 2.5 mg (1) | 3.6 mg (1) | 2.5 mg (1) | 3.6 mg (1) | |
| Size | Storage Time (Months) | 2 mg Triclosan Dispense Amount | 4 mg Triclosan Dispense Amount | 2 mg Triclosan Dispense Amount | 4 mg Triclosan Dispense Amount | Ave UF Increase (%) | 4.2 mg (3/0) Triclosan Dispense Amount | 4.66 mg (3/0) Triclosan Dispense Amount | 4.2 mg (3/0) Triclosan Dispense Amount | 4.66 mg (3/0) Triclosan Dispense Amount | Ave UF Increase (%) |
| 1 | 0 | 2083 | 3491 | 0.0% | 0.0% | 0.0% | 1559 | 2314 | 0.0% | 0.0% | 0.0% |
| 1 | 1 | 4587 | 8492 | 120.2% | 143.3% | 131.7% | 2130 | 2974 | 36.6% | 28.5% | 32.6% |
| 1 | 3 | 5196 | 11593 | 149.4% | 232.1% | 190.8% | 2455 | 3549 | 57.5% | 53.4% | 55.4% |
| 1 | 5 | 5819 | 12497 | 179.4% | 258.0% | 218.7% | 2607 | 3593 | 67.2% | 55.3% | 61.3% |

Example 4

PDS Plus Size 3/0 in Universal Folder Stored at 50° C.

Stability studies were run using size 3/0 PDS Plus® sutures, packaged in universal folders. For each study the finished product was stored at 50° C. for up to 5 months. Samples were tested for triclosan content in the suture and compared to the starting values. Results for these studies are presented below and graphically depicted in FIG. 10.

| | | VAP2005-003 - Uncoated Paper | | | | | VAP2007-058 - Coated Paper | | | | |
|---|---|---|---|---|---|---|---|---|---|---|---|
| | | Triclosan (ppm) | | Percent Increase | | | Triclosan (ppm) | | Percent Increase | | |
| | | | | | | | 2.5 mg (1) | 3.6 mg (1) | 2.5 mg (1) | 3.6 mg (1) | |
| Size | Storage Time (Months) | 2 mg Triclosan Dispense Amount | 4 mg Triclosan Dispense Amount | 2 mg Triclosan Dispense Amount | 4 mg Triclosan Dispense Amount | Ave UF Increase (%) | 4.2 mg (3/0) Triclosan Dispense Amount | 4.66 mg (3/0) Triclosan Dispense Amount | 4.2 mg (3/0) Triclosan Dispense Amount | 4.66 mg (3/0) Triclosan Dispense Amount | Ave UF Increase (%) |
| 3/0 | 0 | 5661 | 6577 | 0.0% | 0.0% | 0.0% | 5236 | 5590 | 0.0% | 0.0% | 0.0% |
| 3/0 | 1 | 10380 | 17325 | 83.4% | 163.4% | 123.4% | 7850 | 8882 | 49.9% | 58.9% | 54.4% |
| 3/0 | 3 | 11563 | 23934 | 104.3% | 263.9% | 184.1% | 8747 | 9824 | 67.0% | 75.7% | 71.4% |
| 3/0 | 5 | 11291 | 23697 | 99.5% | 260.3% | 179.9% | 8928 | 10210 | 70.5% | 82.6% | 76.6% |

Example 5

PDS Plus Size 1 in Relay Tray Stored at 25° C.

Stability studies were run using size 1 PDS Plus® sutures, packaged in relay trays of the type shown in FIGS. 2-5. For each study the finished product was stored at 25° C. for up to 24 months. Samples were tested for triclosan content in the suture and compared to the starting values. Results for these studies are presented below and graphically depicted in FIG. 11.

| | | | VAP2005-003 - Uncoated Paper | | | | | | |
|---|---|---|---|---|---|---|---|---|---|
| | | | Triclosan (ppm) | | | Percent Increase | | | |
| Size | Storage Time (Months) | Storage Temp. (° C.) | 3 mg Triclosan Dispense Amount | 5 mg Triclosan Dispense Amount | 7 mg Triclosan Dispense Amount | 3 mg Triclosan Dispense Amount | 5 mg Triclosan Dispense Amount | 7 mg Triclosan Dispense Amount | Ave Relay Increase (%) |
| 1 | 0 | BL | 1624 | 2682 | 3132 | 0.0% | 0.0% | 0.0% | 0.0% |
| 1 | 1 | 25 | 1538 | 2450 | 3163 | −5.3% | −8.7% | 1.0% | −4.3% |
| 1 | 3 | 25 | 1779 | 2766 | 3609 | 9.5% | 3.1% | 15.2% | 9.3% |
| 1 | 5 | 25 | 2224 | 2947 | 4006 | 36.9% | 9.9% | 27.9% | 24.9% |
| 1 | 7 | 25 | | | | | | | |
| 1 | 9 | 25 | 2091 | 3381 | 4437 | 28.8% | 26.1% | 41.7% | 32.2% |

-continued

| | | | | | | | | |
|---|---|---|---|---|---|---|---|---|
| 1 | 12 | 25 | 2275 | 4225 | 5137 | 40.1% | 57.5% | 64.0% | 53.9% |
| 1 | 15 | 25 | | | | | | | |
| 1 | 18 | 25 | 2810 | 4784 | 5560 | 73.0% | 78.4% | 77.5% | 76.3% |
| 1 | 24 | 25 | 3187 | 4917 | 6532 | 96.2% | 83.3% | 108.6% | 96.0% |

| | VAP2007-054 - Coated Paper | | | | | | |
|---|---|---|---|---|---|---|---|
| | Triclosan (ppm) | | | Percent Increase | | | |
| Size | 3.1 mg) Triclosan Dispense Amount | 3.6 mg Triclosan Dispense Amount | 4.1 mg Triclosan Dispense Amount | 3.1 mg) Triclosan Dispense Amount | 3.6 mg Triclosan Dispense Amount | 4.1 mg Triclosan Dispense Amount | Ave UF Increase (%) |
| 1 | 1751 | 1821 | 2093 | 0.0% | 0.0% | 0.0% | 0.0% |
| 1 | 1763 | 1723 | 2272 | 0.7% | −5.4% | 8.6% | 1.3% |
| 1 | 1960 | 1989 | 2324 | 11.9% | 9.2% | 11.0% | 10.7% |
| 1 | 1698 | 1913 | 2461 | 8.4% | 5.1% | 17.6% | 10.3% |
| 1 | 2088 | 2109 | 2603 | 19.2% | 15.8% | 24.4% | 19.8% |
| 1 | 2109 | 2166 | 2544 | 20.4% | 18.9% | 21.5% | 20.3% |
| 1 | 2226 | 2364 | 2656 | 27.1% | 29.8% | 26.9% | 27.9% |
| 1 | 2360 | 2416 | 2887 | 34.8% | 32.7% | 37.9% | 35.1% |
| 1 | | | | | | | |
| 1 | | | | | | | |

Example 6

PDS Plus Size 3/0 in Relay Tray Stored at 25° C.

Stability studies were run using size 3/0 PDS Plus® sutures, packaged in relay trays of the type shown in FIGS. 2-5. For each study the finished product was stored at 25° C. for up to 24 months. Samples were tested for triclosan content in the suture and compared to the starting values. Results for these studies are presented below and graphically depicted in FIG. 12.

| | | | VAP2005-003 - Uncoated Paper | | | | | | |
|---|---|---|---|---|---|---|---|---|---|
| | | | Triclosan (ppm) | | | Percent Increase | | | |
| Size | Storage Time (Months) | Storage Temp. (° C.) | 3 mg Triclosan Dispense Amount | 5 mg Triclosan Dispense Amount | 7 mg Triclosan Dispense Amount | 3 mg Triclosan Dispense Amount | 5 mg Triclosan Dispense Amount | 7 mg Triclosan Dispense Amount | Ave Relay Increase (%) |
| 3/0 | 0 | BL | 3020 | 4510 | 6851 | 0.0% | 0.0% | 0.0% | 0.0% |
| 3/0 | 1 | 25 | 3376 | 5371 | 7585 | 11.8% | 19.1% | 10.7% | 13.9% |
| 3/0 | 3 | 25 | 3720 | 6074 | 8330 | 23.2% | 34.7% | 21.6% | 26.5% |
| 3/0 | 5 | 25 | 4004 | 6858 | 8783 | 32.6% | 52.1% | 28.2% | 37.6% |
| 3/0 | 7 | 25 | | | | | | | |
| 3/0 | 9 | 25 | 4961 | 7667 | 10570 | 64.3% | 70.0% | 54.3% | 62.9% |
| 3/0 | 12 | 25 | 5237 | 7670 | 11298 | 73.4% | 70.1% | 64.9% | 69.5% |
| 3/0 | 15 | 25 | | | | | | | |
| 3/0 | 18 | 25 | 5930 | 9471 | 13180 | 96.4% | 110.0% | 92.4% | 99.6% |
| 3/0 | 24 | 25 | 6238 | 10213 | 13941 | 106.6% | 126.5% | 103.5% | 112.2% |

| | VAP2007-054 - Coated Paper | | | | | | |
|---|---|---|---|---|---|---|---|
| | Triclosan (ppm) | | | Percent Increase | | | |
| Size | 3.7 mg Triclosan Dispense Amount | 4.2 mg Triclosan Dispense Amount | 4.7 mg Triclosan Dispense Amount | 3.7 mg Triclosan Dispense Amount | 4.2 mg Triclosan Dispense Amount | 4.7 mg Triclosan Dispense Amount | Ave UF Increase (%) |
| 3/0 | 2915 | 3548 | 5112 | 0.0% | 0.0% | 0.0% | 0.0% |
| 3/0 | 3112 | 4140 | 5335 | 6.8% | 16.7% | 4.4% | 9.3% |
| 3/0 | 3500 | 4185 | 5823 | 20.1% | 18.0% | 13.9% | 17.3% |
| 3/0 | 3775 | 4284 | 5699 | 29.5% | 20.7% | 11.5% | 20.6% |
| 3/0 | 4060 | 4839 | 6123 | 39.3% | 36.4% | 19.8% | 31.8% |
| 3/0 | 4351 | 5056 | 6504 | 49.3% | 42.5% | 27.2% | 39.7% |
| 3/0 | 4555 | 5520 | 6644 | 56.3% | 55.5% | 30.0% | 47.3% |
| 3/0 | 4798 | 5600 | 7273 | 64.6% | 57.8% | 42.3% | 54.9% |
| 3/0 | | | | | | | |
| 3/0 | | | | | | | |

Example 7

PDS Plus Size 1 in Relay Tray Stored at 50° C.

Stability studies were run using size 1 PDS Plus® sutures, packaged in relay trays of the type shown in FIGS. 2-5. For each study the finished product was stored at 50° C. for up to 5 months. Samples were tested for triclosan content in the suture and compared to the starting values. Results for these studies are presented below and graphically depicted in FIG. 13.

| | | | VAP2005-003 - Uncoated Paper | | | | | | |
|---|---|---|---|---|---|---|---|---|---|
| | | | Triclosan (ppm) | | | Percent Increase | | | |
| Size | Storage Time (Months) | Storage Temp. (° C.) | 3 mg Triclosan Dispense Amount | 5 mg Triclosan Dispense Amount | 7 mg Triclosan Dispense Amount | 3 mg Triclosan Dispense Amount | 5 mg Triclosan Dispense Amount | 7 mg Triclosan Dispense Amount | Ave Relay Increase (%) |
| 1 | 0 | BL | 1624 | 2682 | 3132 | 0.0% | 0.0% | 0.0% | 0.0% |
| 1 | 1 | 50 | 2784 | 4904 | 6517 | 71.4% | 82.8% | 108.1% | 87.5% |
| 1 | 3 | 50 | 3779 | 6761 | 8866 | 132.7% | 152.1% | 183.1% | 156.0% |
| 1 | 5 | 50 | 4635 | 7325 | 9892 | 185.4% | 173.1% | 215.8% | 191.5% |

| | VAP2007-054 - Coated Paper | | | | | | |
|---|---|---|---|---|---|---|---|
| | Triclosan (ppm) | | | Percent Increase | | | |
| Size | 3.1 mg Triclosan Dispense Amount | 3.6 mg Triclosan Dispense Amount | 4.1 mg Triclosan Dispense Amount | 3.1 mg Triclosan Dispense Amount | 3.6 mg Triclosan Dispense Amount | 4.1 mg Triclosan Dispense Amount | Ave UF Increase (%) |
| 1 | 1751 | 1821 | 2093 | 0.0% | 0.0% | 0.0% | 0.0% |
| 1 | 2734 | 2793 | 3516 | 56.1% | 53.4% | 68.0% | 59.2% |
| 1 | 3174 | 3673 | 4209 | 81.3% | 101.7% | 101.1% | 94.7% |
| 1 | 3471 | 3894 | 4549 | 98.2% | 113.8% | 117.3% | 109.8% |

Example 8

PDS Plus Size 3/0 in Relay Tray Stored at 50° C.

Stability studies were run using size 3/0 PDS Plus® sutures, packaged in relay trays of the type shown in FIGS. 2-5. For each study the finished product was stored at 50° C. for up to 5 months. Samples were tested for triclosan content in the suture and compared to the starting values. Results for these studies are presented below and graphically depicted in FIG. 14.

| | | | VAP2005-003 - Uncoated Paper | | | | | | |
|---|---|---|---|---|---|---|---|---|---|
| | | | Triclosan (ppm) | | | Percent Increase | | | |
| Size | Storage Time (Months) | Storage Temp. (° C.) | 3 mg Triclosan Dispense Amount | 5 mg Triclosan Dispense Amount | 7 mg Triclosan Dispense Amount | 3 mg Triclosan Dispense Amount | 5 mg Triclosan Dispense Amount | 7 mg Triclosan Dispense Amount | Ave Relay Increase (%) |
| 3/0 | 0 | BL | 3020 | 4510 | 6851 | 0.0% | 0.0% | 0.0% | 0.0% |
| 3/0 | 1 | 50 | 5125 | 8790 | 12016 | 69.7% | 94.9% | 75.4% | 80.0% |
| 3/0 | 3 | 50 | 6625 | 10312 | 13543 | 119.4% | 128.6% | 97.7% | 115.2% |
| 3/0 | 5 | 50 | 6376 | 11061 | 14604 | 111.1% | 145.3% | 113.2% | 123.2% |

| | VAP2007-054 - Coated Paper | | | | | | |
|---|---|---|---|---|---|---|---|
| | Triclosan (ppm) | | | Percent Increase | | | |
| Size | 3.7 mg Triclosan Dispense Amount | 4.2 mg Triclosan Dispense Amount | 4.7 mg Triclosan Dispense Amount | 3.7 mg Triclosan Dispense Amount | 4.2 mg Triclosan Dispense Amount | 4.7 mg Triclosan Dispense Amount | Ave UF Increase (%) |

-continued

| | | | | | | | |
|---|---|---|---|---|---|---|---|
| 3/0 | 2915 | 3548 | 5112 | 0.0% | 0.0% | 0.0% | 0.0% |
| 3/0 | 5725 | 6750 | 8313 | 96.4% | 90.2% | 62.6% | 83.1% |
| 3/0 | 6667 | 7903 | 9436 | 128.7% | 122.7% | 84.6% | 112.0% |
| 3/0 | 6913 | 8189 | 9482 | 137.2% | 130.8% | 85.5% | 117.8% |

All patents, test procedures, and other documents cited herein, including priority documents, are fully incorporated by reference to the extent such disclosure is not inconsistent and for all jurisdictions in which such incorporation is permitted.

While the illustrative embodiments disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

Additional Aspects of the Invention

As indicated, a method of increasing the shelf life of a packaged antimicrobial medical device is disclosed and claimed herein. In one embodiment, the adsorbent material is provided by coating the adsorbent material on at least a portion of one surface of the inner package. In another embodiment, the adsorbent material is provided by placing an adsorbent substrate within the outer package. In another embodiment, the adsorbent substrate is formed by coating a substrate with an adsorbent material. In another embodiment, the adsorbent substrate is formed of an adsorbent material. In another embodiment, the inner package comprises a universal envelope formed from a paperboard stock having at least one surface coated with an adsorbent material. In another embodiment, the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin. In another embodiment, the inner package comprises a containment compartment and an outer cover, the outer cover having an one surface coated with an adsorbent material. In another embodiment, the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

As indicated, a packaged antimicrobial suture having improved shelf life is disclosed and claimed herein. In one embodiment, the packaged antimicrobial suture exhibits improved shelf life. In another embodiment, the adsorbent material is provided by coating said adsorbent material on at least a portion of one surface of said inner package. In another embodiment, the adsorbent material is provided by placing an adsorbent substrate within said outer package. In another embodiment, the adsorbent substrate is formed by coating a substrate with an adsorbent material. In another embodiment, the adsorbent substrate is formed of an adsorbent material. In another embodiment, the antimicrobial agent is selected from said group consisting of halogenated hydroxyl ethers, acyloxydiphenyl ethers, and combinations thereof. In another embodiment, the inner package comprises a universal envelope formed from a paperboard stock having one surface coated with an adsorbent material. In another embodiment, the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin. In another embodiment, the inner package comprises a containment compartment and an outer cover, said outer cover having one surface coated with an adsorbent material. In another embodiment, the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

What is claimed:

1. A packaged antimicrobial suture having improved shelf life comprising:
    an inner package having a surface and an antimicrobial agent source loaded with an antimicrobial agent;
    an adsorbent material effective to adsorb a portion of said antimicrobial agent over time;
    a suture positioned within said inner package, said suture comprising one or more surfaces; and
    an outer package having an inner surface, said outer package having said inner package positioned within;
    wherein said suture, said inner package and said inner surface of said outer package are subjected to time, temperature and pressure conditions sufficient to vapor transfer an effective amount of said antimicrobial agent from said antimicrobial agent source to said surface of said suture and said surface of said inner package, to substantially inhibit bacterial colonization on said suture and said inner package.

2. The packaged antimicrobial suture of claim 1, wherein the adsorbent material is coated on at least a portion of one surface of the inner package.

3. The packaged antimicrobial suture of claim 1, wherein the adsorbent material is an adsorbent substrate within the outer package.

4. The packaged antimicrobial suture of claim 3, wherein the adsorbent substrate is a substrate coated with the adsorbent material.

5. The packaged antimicrobial suture of claim 3, wherein the adsorbent substrate is formed of the adsorbent material.

6. The packaged antimicrobial suture of claim 1, wherein the suture positioned within the inner package is coated with the antimicrobial agent.

7. The packaged antimicrobial suture of claim 1, wherein the antimicrobial agent is selected from the group consisting of halogenated hydroxyl ethers, acyloxydiphenyl ethers, and combinations thereof.

8. The packaged antimicrobial suture of claim 1, wherein the effective amount of the antimicrobial agent is transferred from the source of antimicrobial agent to the suture and the inner package during an ethylene oxide sterilization process.

9. The packaged antimicrobial suture of claim 1, wherein the inner package comprises a universal envelope formed from a paperboard stock having at least one surface coated with the adsorbent material.

10. The packaged antimicrobial suture of claim 9, wherein the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

11. The packaged antimicrobial suture of claim 1, wherein the inner package comprises a containment compartment and an outer cover, the outer cover having a surface coated with the adsorbent material.

12. The packaged antimicrobial suture of claim 11, wherein the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

13. A packaged medical device comprising:
an inner package having a surface and an antimicrobial agent source loaded with an antimicrobial agent;
an adsorbent material effective to adsorb a portion of said antimicrobial agent over time;
a medical device positioned within said inner package, said medical device comprising one or more surfaces; and
an outer package having an inner surface, said outer package having said inner package positioned within;
wherein said medical device, said inner package and said inner surface of said outer package are subjected to time, temperature and pressure conditions sufficient to vapor transfer an effective amount of said antimicrobial agent from said antimicrobial agent source to said surface of said medical device and said surface of said inner package, to substantially inhibit bacterial colonization on said suture and said inner package.

14. The packaged medical device of claim 13, wherein the adsorbent material is coated on at least a portion of one surface of the inner package.

15. The packaged medical device of claim 13, wherein the adsorbent material is an adsorbent substrate within the outer package.

16. The packaged medical device of claim 15, wherein the adsorbent substrate is a substrate coated with the adsorbent material.

17. The packaged medical device of claim 15, wherein the adsorbent substrate is formed of the adsorbent material.

18. The packaged medical device of claim 13, wherein the medical device positioned within the inner package is coated with the antimicrobial agent.

19. The packaged medical device of claim 13, wherein the antimicrobial agent is selected from the group consisting of halogenated hydroxyl ethers, acyloxydiphenyl ethers, and combinations thereof.

20. The packaged medical device of claim 13, wherein the effective amount of the antimicrobial agent is transferred from the source of antimicrobial agent to the medical device and the inner package during an ethylene oxide sterilization process.

21. The packaged medical device of claim 13, wherein the inner package comprises a universal envelope formed from a paperboard stock having at least one surface coated with the adsorbent material.

22. The packaged antimicrobial suture of claim 21, wherein the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

23. The packaged medical device of claim 13, wherein the inner package comprises a containment compartment and an outer cover, the outer cover having a surface coated with the adsorbent material.

24. The packaged medical device of claim 22, wherein the adsorbent material is selected from bentonite, activated carbon, activated alumina, silica gel, zeolite, super-absorbant polymers, humectants, polymeric coatings, ground polymeric coatings, natural products, non-paper substrates, and clays, including kaolin.

\* \* \* \* \*